(12) United States Patent
Oomens et al.

(10) Patent No.: US 7,588,770 B2
(45) Date of Patent: *Sep. 15, 2009

(54) RECOMBINANT VIRUSES OF THE PARAMYXOVIRIDAE FAMILY WITH HETEROLOGOUS ENVELOPE GLYCOPROTEINS

(75) Inventors: Antonius G. P. Oomens, Charlottesville, VA (US); Gail W. Wertz, King George, VA (US); Alexander George Megaw, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/575,279

(22) PCT Filed: Dec. 10, 2004

(86) PCT No.: PCT/US2004/041067

§ 371 (c)(1),
(2), (4) Date: Apr. 11, 2006

(87) PCT Pub. No.: WO2005/080417

PCT Pub. Date: Sep. 1, 2005

(65) Prior Publication Data

US 2007/0104734 A1    May 10, 2007

Related U.S. Application Data

(60) Provisional application No. 60/528,214, filed on Dec. 10, 2003, provisional application No. 60/588,379, filed on Jul. 16, 2004.

(51) Int. Cl.
*A61K 39/38* (2006.01)
*A61K 39/12* (2006.01)
*A61K 39/295* (2006.01)
*A61K 39/155* (2006.01)

(52) U.S. Cl. .............. 424/211.1; 424/199.1; 424/202.1; 424/184.1

(58) Field of Classification Search ........................ None
See application file for complete search history.

(56) References Cited

FOREIGN PATENT DOCUMENTS

| WO | WO 01/04335 A2 | | 1/2001 |
|---|---|---|---|
| WO | WO 02/09749 A2 | * | 2/2002 |
| WO | WO 03/029416 A2 | | 4/2003 |
| WO | WO 03/072720 A2 | | 9/2003 |

OTHER PUBLICATIONS

Sastre et al., The stability of human respiratory syncytial virus is enhanced by incorporation of the baculovirus GP64 protein, 2007, Vaccine, vol. 25, pp. 5025-5033.*

Gupta et al., "Stabilization of respiratory syncytial virus (RSV) against thermal inactivation and freeze-thaw cycles for development and control of RSV vaccines and immune globulin", Vaccine, Butterworth Scientific. Guildford, GB, vol. 14, No. 15, Oct. 1996, pp. 1417-1420.

International Search Report dated Apr. 5, 2006.

* cited by examiner

*Primary Examiner*—Gary B Nickol
*Assistant Examiner*—Benjamin P Blumel
(74) *Attorney, Agent, or Firm*—Nixon Peabody, LLP

(57) ABSTRACT

The invention provides recombinant viruses comprising heterologous envelope proteins capable of mediating entry of the recombinant viruses into host cells. In one embodiment, a recombinant virus of the invention is a member of the *Paramyx-ovirzdae* family (e.g., a respiratory syncytial virus), and the heterologous envelope protein includes the ectodomain of a baculovirus envelope protein (e.g., the GP64 protein). In some cases, the heterologous envelope protein is provided in addition to homologous envelope proteins) which may or may not be functional. The heterologous protein can provide the recombinant virus with enhanced stability (e.g., at 4° C., 22° C., or 37° C.), and allows production of high-titer virus stocks. The heterologous protein can also impart temperature sensitivity to the replication of the recombinant virus. In addition, the recombinant virus can be designed to be infectious but incapable of spreading between host cells by providing the heterologous protein by complementation in trans. These features attenuate the disease-causing potential of the recombinant virus, therefore increasing its safety of use as vaccines.

9 Claims, 17 Drawing Sheets

FIGURE 1

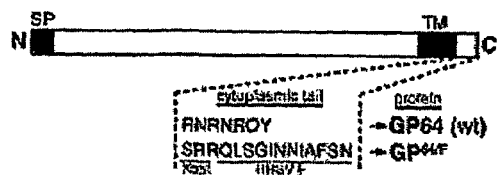
FIGURE 3A
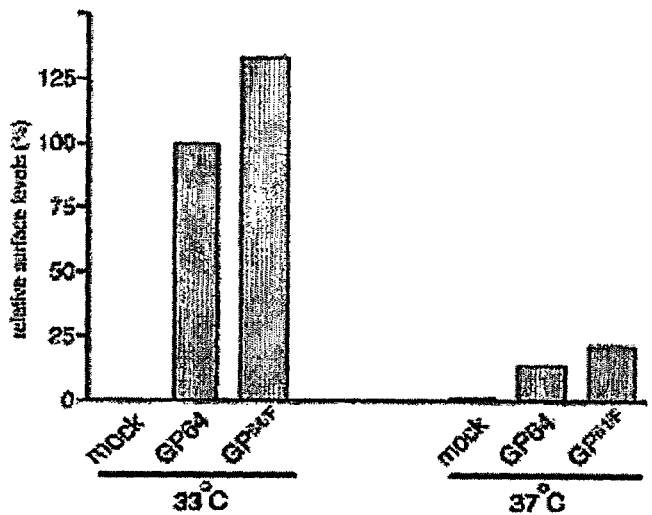
FIGURE 3B
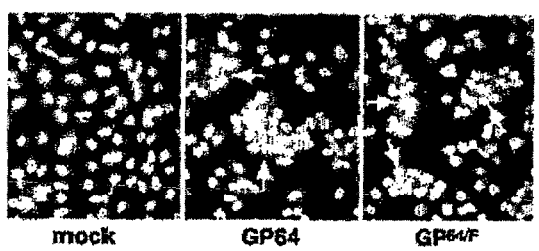
FIGURE 3C
FIGURE 3D

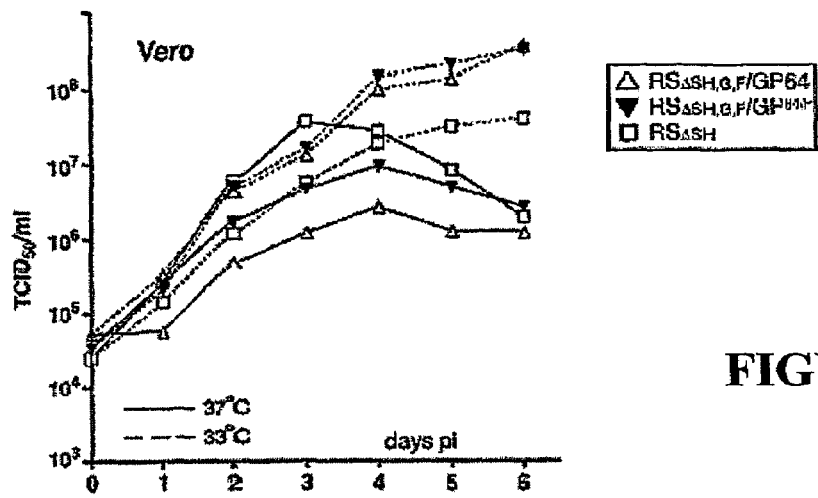
FIGURE 8A
FIGURE 8B
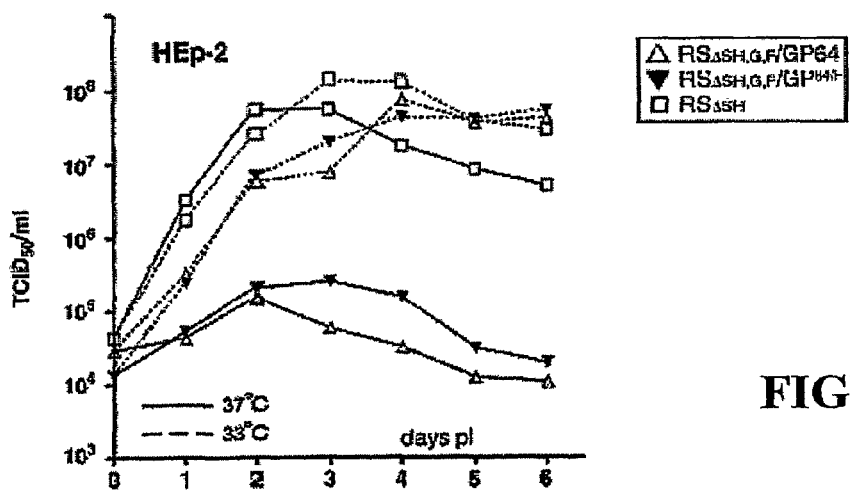
FIGURE 8C

Vero  Vbac

Figure 16

RECOMBINANT VIRUSES OF THE PARAMYXOVIRIDAE FAMILY WITH HETEROLOGOUS ENVELOPE GLYCOPROTEINS

RELATED APPLICATONS

This application is a 371 of PCT/US04/41067, filed Dec. 10, 2004, which claims benefit of U.S. Provisional Application Ser. No. 60/528,214, filed on Dec. 10, 2003, and U.S. Provisional Application Ser. No. 60/588,379, filed on Jul. 16, 2004, which are incorporated entirely herein.

GOVERNMENT INTERESTS

This invention was produced at least in part using funds obtained from United States Public Health Service Grant AI20181 from the National Institutes of Health. Consequently, the United States government may have certain rights in this invention.

FIELD OF THE INVENTION

The invention relates to recombinant viruses comprising heterologous envelope proteins.

BACKGROUND OF THE INVENTION

Human respiratory syncytial virus (HRSV) is a major cause of severe lower respiratory tract disease in infants and children worldwide as well as in immunosuppressed individuals and the elderly. Amidst ongoing efforts to develop human respiratory syncytial virus specific vaccines and therapeutic agents, prevention and treatment of human respiratory syncytial virus disease remain a significant challenge. Human respiratory syncytial virus is the type species of the genus *Pneumovirus* within the family *Paramyxoviridae* and contains a negative-sense, single-stranded RNA genome that expresses eleven known proteins from ten genes. Three proteins, SH (small hydrophobic), G (attachment), and F (fusion), have been characterized as transmembrane glycoproteins and are detected in purified virions. On the surface of infected cells, the G and F proteins concentrate in cell-associated, virus-induced filamentous structures with variable lengths of up to 10 μm. The G and F proteins contain the major antigenic epitopes of human respiratory syncytial virus, and their roles in the anti-HRSV imnune response have been investigated extensively.

The SH protein is a small integral membrane protein of unknown function, with a relatively low amino acid conservation among human respiratory syncytial virus strains. Previous studies indicate that SH is dispensable for human respiratory syncytial virus growth in cell culture, and its absence has little impact on the ability of the virus to replicate in the respiratory tracts of mice and chimpanzees.

The G gene of human respiratory syncytial virus expresses both a type II membrane-anchored glycoprotein and a soluble protein. G protein is heavily O-glycosylated and shows significant structural similarities to mucinous proteins. The G protein was initially characterized as providing an attachment function, and domains in G have since been identified that bind to sulfated glycosaminoglycans on the cell surface in vitro. The requirement for G protein in infectivity in cell culture varies depending on the cell type. Both a cold-adapted virus in which most of the sequence encoding the SH and G proteins is absent, and an engineered virus lacking the G gene replicate efficiently in Vero cells. However, replication of these G-deleted viruses is significantly impaired in HEp-2 cells as well as in mice, cotton rats, and humans.

The fusion protein, F, is a type I transmembrane glycoprotein that mediates the formation of syncytia typically observed in human respiratory syncytial virus infected cells. F protein is thought to direct entry of human respiratory syncytial virus at the plasma membrane in a pH-independent manner. Among the transmembrane glycoproteins, F appears to be a critical component for virus transmission, as F, matrix (M) protein, and the nucleocapsid were found to be the minimal requirements for production of infectious particles, and viruses that express F as the only glycoprotein propagated efficiently in Vero cells.

A previous attempt to vaccinate young children against respiratory syncytial virus (RSV) employed a parenterally administered formalin-inactivated RSV vaccine. Unfortunately, administration of this vaccine in several field trials was shown to be associated with the development of a significantly exacerbated illness following subsequent natural infection with RSV.

Following the lack of success with the formalin-inactivated RSV vaccine, emphasis was placed on the development of live attenuated vaccines. For example, cold adaptation, a process by which virus is adapted to grow at temperatures colder than those at which it normally optimally grows, has been used to develop temperature sensitive, attenuated RSV mutants for consideration as vaccines (Maassab, et al., VACCINE, 3:355-369 (1985)).

In most cases, the attenuated RSV, like the wild-type RSV, is unstable above 0° C. The attempt to store RSV stocks below 0° C. is also unsuccessful, partially because of the sensitivity of RSV to freezing and thawing. Moreover, storing virus stocks under 0° C. requires elaborate and expensive cold chain equipment, which significantly increases the cost associated with the use of RSV as a vaccine. Furthermore, the instability of RSV presents a challenge for producing high-titer RSV vaccines.

SUMMARY OF THE INVETION

The invention features recombinant viruses comprising heterologous envelope proteins. In many embodiments, the heterologous envelope proteins stabilize the infectivity of the recombinant viruses, and allow production of high-titer virus stocks. These features permit storage and transportation of the recombinant viruses without employing special cold chain equipment, and may eventually lead to improved potency and effectiveness of the virus vaccines. In many other embodiments, the heterologous envelope proteins confer temperature sensitivity upon the recombinant viruses. In addition, the recombinant viruses can be infectious but incapable of spreading between host cells. These advantages attenuate the disease-causing potential of the recombinant viruses, therefore increasing their safety of use as vaccines or therapeutic vectors.

In accordance with one aspect of the invention, the recombinant virus is a recombinant paramyxovirus comprising a nonparamyxoviral envelope protein which is capable of mediating entry of the paramyxovirus into a mammalian cell. As used herein, "paramyxovirus" includes all members of the *Paramyxoviridae* family. The *Pararnyxoviridae* family includes the sub-family *Paramyxovirinae* and the sub-family *Pneumovirinae*. Exemplary paramyxoviruses include, but are not limited to, parainfluenza virus type I, II, or III, respiratory syncytial viruses, measles viruses, and mumps viruses.

In one embodiment, the recombinant paramyxovirus is a respiratory syncytial virus, such as HRSV, and the nonparamyxoviral envelope protein includes the ectodomain of an envelope protein of a member of the family Baculoviridae. Exemplary baculovirus envelope proteins include, but are not limited to, the GP64 protein and its functional equivalents thereof. In one example, the nonparamyxoviral envelope protein includes a full-length baculovirus GP64 protein, such as a full-length GP64 protein of AcMNPV. In another example, the nonparamyxoviral envelope protein includes the ectodomain and the transmembrane domain of a baculovirus GP64 protein, and the cytoplasmic tail domain (or a fragment thereof) of the respiratory syncytial virus fusion protein F.

In another embodiment, the recombinant virus of the invention has improved stability of infectivity compared to its wild-type counterpart. For instance, the recombinant virus can be stored under specified storage conditions for a substantial period of time without significantly losing infectivity. Preferably, the infectivity of the recombinant virus at the end of the storage period retains at least 50%, 55%, 60%, 65%, 70%, 75%, 80%, 85%, 90%, 95%, or more of the original infectivity measured at the beginning of the storage period. The storage period can be at least 1 day, 2 days, 3 days, 4 days, 5 days, 6 days, 1 week, 2 weeks, 3 weeks, 4 weeks, 1 month, 2 month, or longer. The storage conditions may include, for example, keeping the storage temperature or temperatures at above 0° C. (e.g., at 4° C., 10° C., 15° C., room temperature, or 37° C.). Under the same storage conditions, the infectivity of a wild-type virus (e.g., HRSV A2 strain, or a counterpart wild-type virus from which the recombinant virus can be derived) is reduced to less than 50%, 45%, 40%, 35%, 30%, 25%, 20%, 15%, 10%, 5%, or less of the original infectivity measured at the beginning of the storage period.

In one example, the storage conditions include maintaining the recombinant paramyxovirus at above 0° C. (e.g., room temperature or 37° C.) cumulatively for at least 3.5 days, such as at least 1 week, 2 weeks, or 1 month. The storage conditions may include one or more freezing or thawing steps. In many cases, the storage conditions do not include any freezing or thawing step.

In yet another embodiment, the recombinant virus of the invention includes or encodes one or more immunogenic epitopes of a human pathogen. The pathogen is capable of causing a human disease or a medical syndrome. The pathogen can be selected, for example, from viruses, bacteria, protozoa, fungi, and parasites. Administration of the recombinant paramyxovirus into a human subject can elicit an immune response against the pathogen or a component thereof.

In still yet another embodiment, the recombinant virus includes or encodes immunogenic epitopes of two or more different human pathogens. Each of these human pathogens can cause a different respective human disease or medical syndrome.

In a further embodiment, the recombinant virus is infectious but cannot spread between human cells. In one example, the recombinant virus does not include any functional homologous envelope protein that can mediate viral entry into host cells. The homologous envelope protein(s) can be deleted from the viral genome, or deactivated by mutations or modifications.

In another embodiment, the recombinant virus includes a non-naturally occurring RSV fusion protein F. In many instances, the non-naturally occurring RSV fusion protein F includes a heterologous cytoplasmic tail or transmembrane domain. In one example, the heterologous cytoplasmic tail or transmembrane domain is derived from vesicular stomatitis Indiana virus (VSIV) G protein. In another example, the heterologous cytoplasmic tail or transmembrane domain includes a chimeric sequence comprising both VSIV G protein and RSV fusion protein F sequences. In some instances, the non-naturally occurring RSV fusion protein F does not have any cytoplasmic tail domain.

In yet another embodiment, the recombinant virus of the invention is incapable of replicating, transcribing, or translating in infected cells. This can be achieved, for example, by deleting or deactivating respective DNA or RNA polymerases.

In still another embodiment, a recombinant paramyxovirus of the invention comprises a nonparamyxoviral envelope protein which confers temperature sensitivity upon the recombinant paramyxovirus. This feature can attenuate the disease potential of the recombinant virus and therefore increase its safety of use as a vaccine or a therapeutic vector (e.g., a gene therapy vector or a viral therapy vector). In one example, the recombinant virus is prepared in large amounts by culturing mammalian cells infected with the virus at about 33° C. (e.g., between 31° C. and 35° C., between 32° C. and 34° C., or between 32.5° C and 33.5° C), and then recovering the virus from the infected cells.

The invention also contemplates pharmaceutical compositions, such as vaccine formulations, that comprise a recombinant virus of the invention. In addition, the invention features methods of administering the vaccine formulations into humans or animals to elicit immune responses against the epitope(s) carried by the recombinant virus.

In accordance with another aspect, the invention provides a method useful for detecting the presence or absence of a molecule or an antibody capable of binding to an epitope of interest. The method includes the steps of contacting a biological sample with a recombinant virus including the epitope of interest, and detecting any binding between the recombinant virus and a molecule or an antibody in the biological sample. Any bound antibody can be recognized, for example, by using a secondary antibody, as appreciated by those skilled in the art.

In yet another aspect, the invention provides polynucleotides which encode each and every component of a recombinant virus of the invention. The polynucleotide can be DNA, RNA, or a modified form thereof. The polynucleotide can be double-stranded or single-stranded (e.g., a positive strand RNA or a negative strand RNA). In one embodiment, recombinant RNA viruses are recovered by expressing a polynucleotide of the invention in cells which are co-transfected with plasmids encoding viral proteins required for transcription and replication of the viral RNA.

The invention also features polynucleotides which encode all of the components of a recombinant paramyxovirus of the invention except the heterologous nonparamyxoviral envelope protein. The heterologous nonparamyxoviral envelope protein can be provided in trans by using a complementation packaging system.

In still yet another aspect, the invention provides mammalian cells or mammals (including humans) which include a recombinant virus of the invention, or one or more polynucleotides that encode all of the components of the recombinant virus.

In one embodiment, a mammalian cell of the invention includes an expression cassette encoding a heterologous envelope protein comprising an ectodomain of a baculovirus transmembrane protein, and one or more expression vectors comprising or encoding the genome of an infection-defective or infection-attenuated mammalian virus. The expression cassette can be stably or transiently transfected or transduced into the mammalian cell. In one example, the expression cassette is integrated into a chromosome of the mammalian cell. In another example, the mammalian cell is a Vero cell.

The infection-defective or -attenuated mammalian virus, when assembled in the mammalian cell, incorporates the heterologous envelope protein which affords the virus with improved infectivity and/or stability. In one example, the mammalian virus is a recombinant RSV, and the heterologous envelope protein comprises an ectodomain of baculovirus envelope GP64 protein. In another example, the recombinant RSV lacks one or more transmembrane proteins, such as SH, G, or F proteins. The recombinant RSV can also include a modified F protein which lacks a homologous cytoplasmic tail or transmembrane domain, or has a heterologous cytoplasmic tail or transmembrane domain.

Furthermore, the invention features mammalian cells, such as Vero cells, that are stably transfected or transduced with an expression cassette encoding a recombinant viral envelope protein. The viral envelope protein includes an ectodomain of a baculovirus transmembrane protein (e.g., the GP64 protein). The invention also features recombinant RSVs comprising a non-naturally occurring RSV fusion protein F. These recombinant RSVs are defective or attenuated for cell-to-cell transmission.

Recombinant mammalian or vertebrate viruses other than paramyxoviruses can be similarly prepared using the present invention. These viruses may have all of the advantageous properties possessed by the recombinant paramyxoviruses of the invention. For instance, these viruses can have improved stability of infectivity as compared to their wild-type counterparts. In addition, these viruses can be temperature sensitive, and infectious but incapable of spreading between host cells. In one embodiment, these viruses include heterologous envelope proteins that comprise the ectodomain of a baculovirus transmembrane protein, such as the GP64 protein or its functional equivalents. In another embodiment, these viruses are not recombinant lentiviruses, such as those described in Kumar, et al., HUM. GENE THER., 14:67-77 (2003); and Ojala, et al., BIOCHEM. BIOPHYS. RES. COMMUN., 284:777-784 (2001).

Other features, objects, and advantages of the invention are apparent in the detailed description that follows. It should be understood, however, that the detailed description, while indicating preferred embodiments of the invention, is given by way of illustration only, not limitation. Various changes and modifications within the scope of the invention will become apparent to those skilled in the art from the detailed description.

BRIEF DESCRIPTION OF THE DRAWINGS

The drawings are provided for illustration, not limitation. The present application also incorporates by reference the entire content of FIG. 10A of U.S Provisional Application Ser. No. 60/588,379, filed on Jul. 16, 2004.

FIG. 1 schematically illustrates the genomes of transmissible recombinant HRSVs.

FIG. 3A depicts the C-terminal region of GP64 and chimeric protein $GP^{64/F}$. In $GP^{64/F}$, the 7-amino acid cytoplasmic tail domain of GP64 (RNRNRQY, SEQ ID NO:1) was replaced by the 12 C-terminal amino acids of the HRSV F protein (QLSGINNIAFSN, amino acid residues 3-15 of SEQ ID NO:2) via an introduced XbaI site. SP denotes signal peptide, and TM represents transmembrane domain.

FIG. 3B shows relative levels of GP64 and $GP^{64/F}$ at the cell surface. HEp-2 cells were transfected with plasmids expressing GP64 and $GP^{64/F}$ or mock transfected, and incubated at 33° C. or 37° C. At 34 h posttransfection, cells were chilled and incubated with anti-GP64 antibody AcVl on ice, and relative protein surface levels determined in duplicate by using CELISA. Expression levels were normalized to that of GP64 at 33° C.

FIG. 3C illustrates the membrane fusion function of GP64 and chimeric protein $GP^{64/F}$. Transfected HEp-2 cells in FIG. 3B were exposed to PBS, pH 5.0, for 3.5 min, incubated in normal growth medium at 33° C. for 4 hours, and fixed with paraformaldehyde. Cells were stained with Hoechst reagent, and examined by fluorescence microscopy (magnification, 400×). Arrows indicate syncytia.

FIG. 3D indicates the pH threshold for membrane fusion. Transfected HEp-2 cells were exposed to PBS, with a pH ranging from 5 to 7, for 3.5 min, and processed as described in FIG. 3C. Syncytia containing at least five nuclei were scored with phase contrast microscopy ('++', >150 syncytia per well; '+', 40-150 syncytia per well; '+/', between 2 and 5 syncytia; '-', no syncytia observed).

Figure 7A:

FIG. 7A is an immunoelectron microscopy (IEM) image of $RS_{\Delta SH,G,F}$/GP64 virus infected cells. Vero cells infected with the engineered virus were fixed at 27 h postinfection, incubated with anti-GP64 antibodies followed by a 6 nm gold-conjugated secondary antibody, and prepared for IEM. Size bar, 100 nm.

Figure 7B:
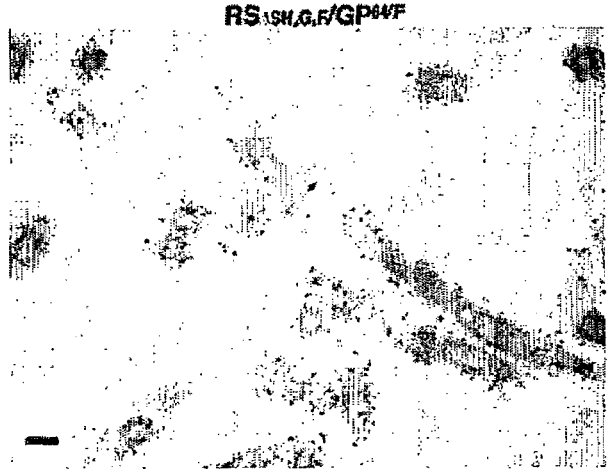

FIG. 7B is an immunoelectron microscopy (IEM) image of $RS_{\Delta SH,G,F}$/GP$^{64/F}$ virus infected cells. Vero cells infected with the engineered virus were fixed at 27 h postinfection, incubated with anti-GP64 antibodies followed by a 6 nm gold-conjugated secondary antibody, and prepared for IEM. Size bar, 100 nm.

Figure 7C:
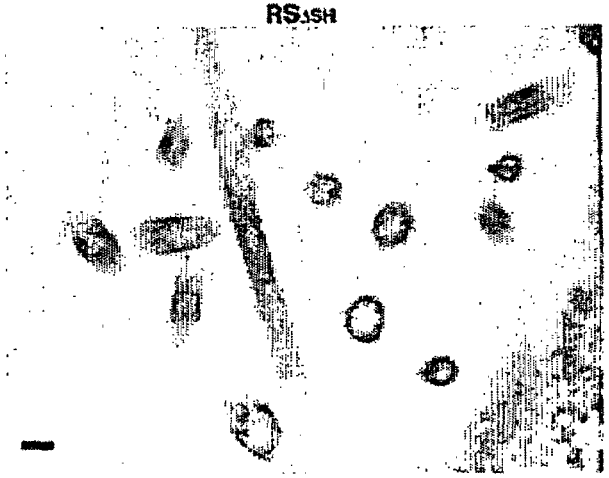

FIG. 7C shows an immunoelectron microscopy (IEM) image of $RS_{\Delta SH}$ virus infected cells. Vero cells infected with the engineered virus were fixed at 27 h postinfection, incubated with anti-GP64 antibodies followed by a 6 nm gold-conjugated secondary antibody, and prepared for IEM. Size bar, 100 mn.

FIG. 8A indicates virus replication in Vero cells at 37° C. and 33° C. Vero cells were infected with the engineered viruses for 1.5 h at 37° C. at a multiplicity of 0.5, washed, and then incubated at 37° C. or 33° C. Immediately after virus adsorption and at 1-day intervals thereafter, cells were scraped into the supernatants and titers of virus suspensions were determined in duplicate by 50% tissue culture infective dose ($TCID_{50}$).

FIG. 8B demonstrates virus replication in HEp-2 cells at 37° C. and 33° C. HEp-2 cells were infected with the engineered viruses for 1.5 h at 37° C. at a multiplicity of 0.5, washed, and then incubated at 37° C. or 33° C. Immediately after virus adsorption and at 1-day intervals thereafter, cells were scraped into the supernatants and titers of virus suspensions were determined in duplicate by $TCID_{50}$.

FIG. 8C compares cell-associated and supernatant-associated infectivities. Vero cells were infected as described in FIG. 8A, and supernatant and cells were harvested separately at 24 and 48 h postinfection (pi). Virus titers were determined in duplicate, and the percentage of infectivity relative to the total (supernatant+cell associated) was calculated (cell, cell-associated infectivity; supt, supernatant-associated infectivity). The values represent the mean percentage of duplicate samples.

Figure 9A:
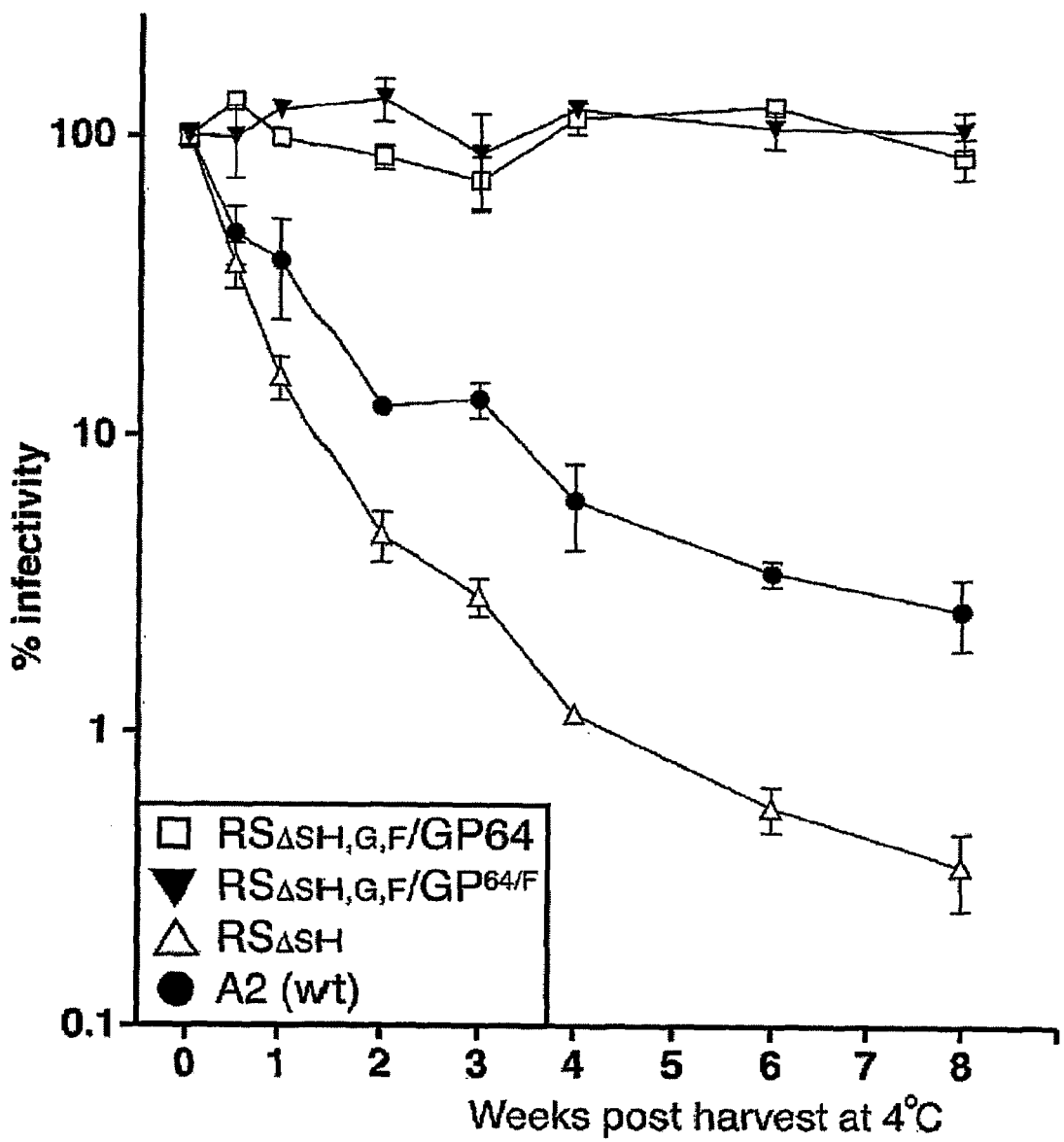

FIG. 9A demonstrates the stability of infectivity of the engineered viruses. Vero cells were infected with viruses $RS_{\Delta SH}$, $RS_{\Delta SH,G,F}$/GP$^{64/F}$, $RS_{\Delta SH,G,F}$/GP64, or wild-type A2, and stocks were generated by scraping cells into the supernatant followed by gentle pipetting and removal of cell debris. Stocks were aliquotted and stored at 4° C. Titers were determined by $TCID_{50}$ at the day of harvest, after 3.5 days, and at weekly intervals thereafter. Infectivities were plotted as a percentage of the $TCID_{50}$ at the start of the experiment (week 0). Error bars represent standard deviations from the mean of triplicate samples.

Figure 9B:
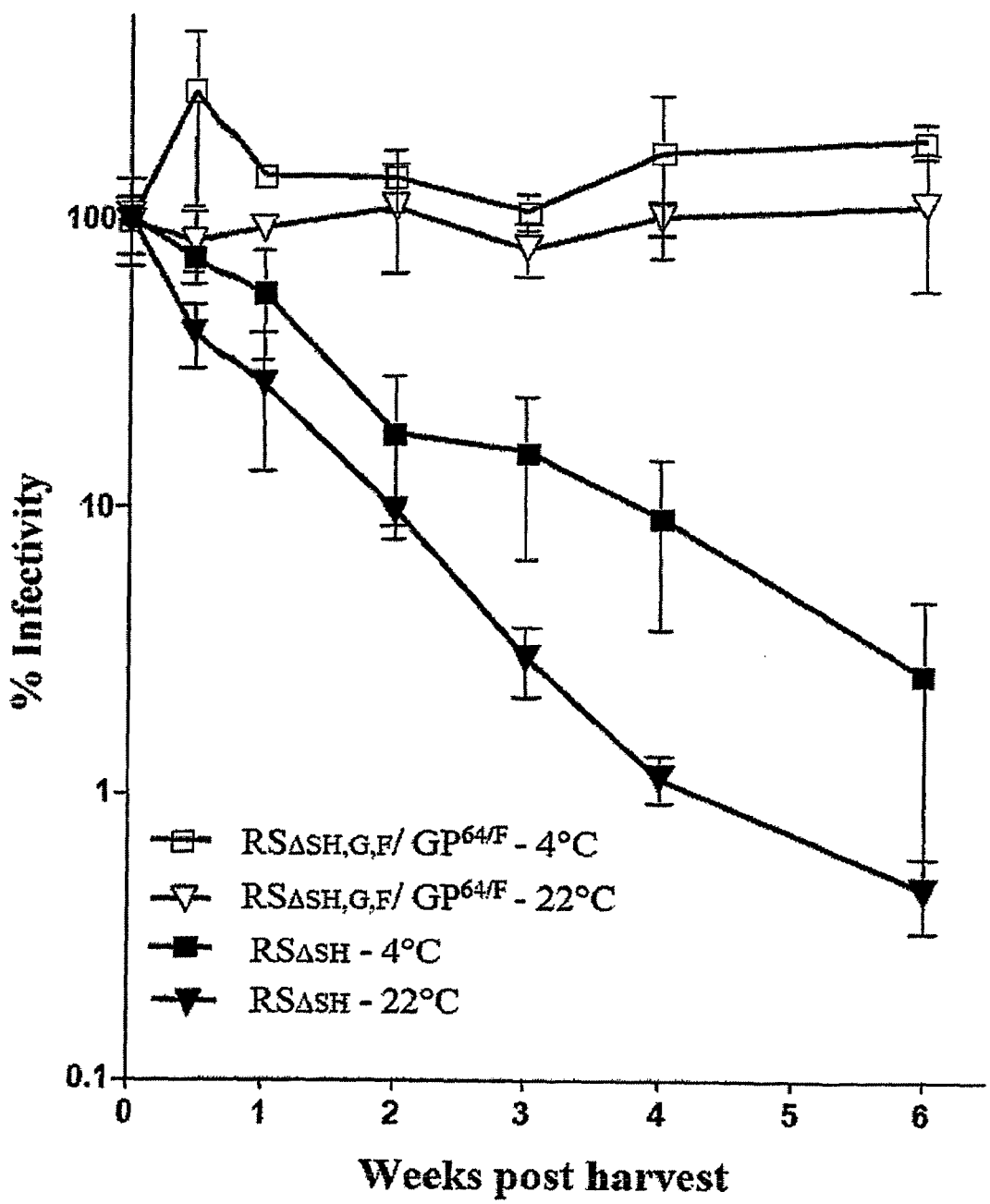

FIG. 9B compares the stability of viruses $RS_{\Delta SH}$ and $RS_{\Delta SHG,F}$/GP$^{64/F}$ at 4° C. and 22° C.

Figure 10A:
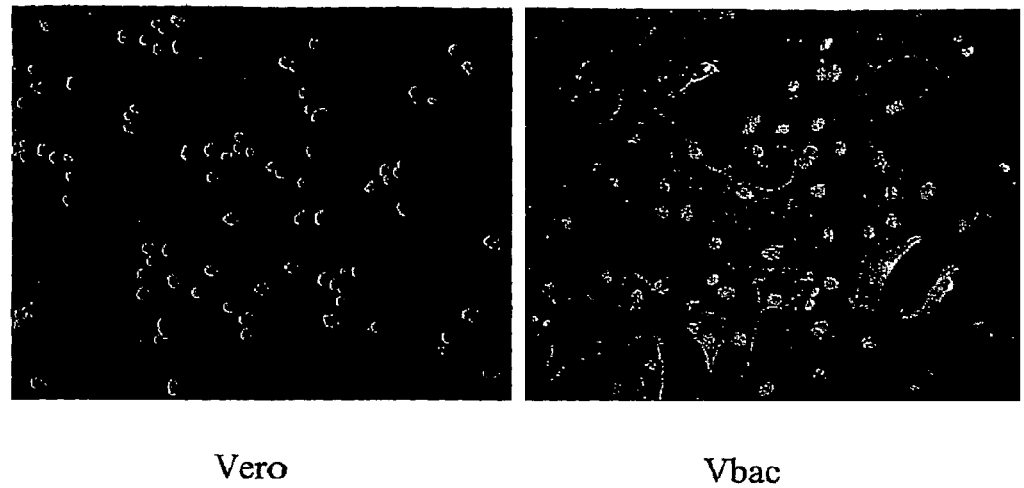

FIG. 10A illustrates GP$^{64/F}$ surface expression in Vero and Vbac (pass 8) cells detected by using indirect immunofluorescence. Vbac or Vero cells were incubated with anti-GP64 MAb AcV1 on ice, washed, and fixed with 4% paraformaldehyde. Cells were then incubated with an alexa-594-conjugated secondary antibody (red), stained with Hoechst to visualize nuclei (blue), and examined with fluorescence microscopy (magnification, ×400).

Figure 10B:
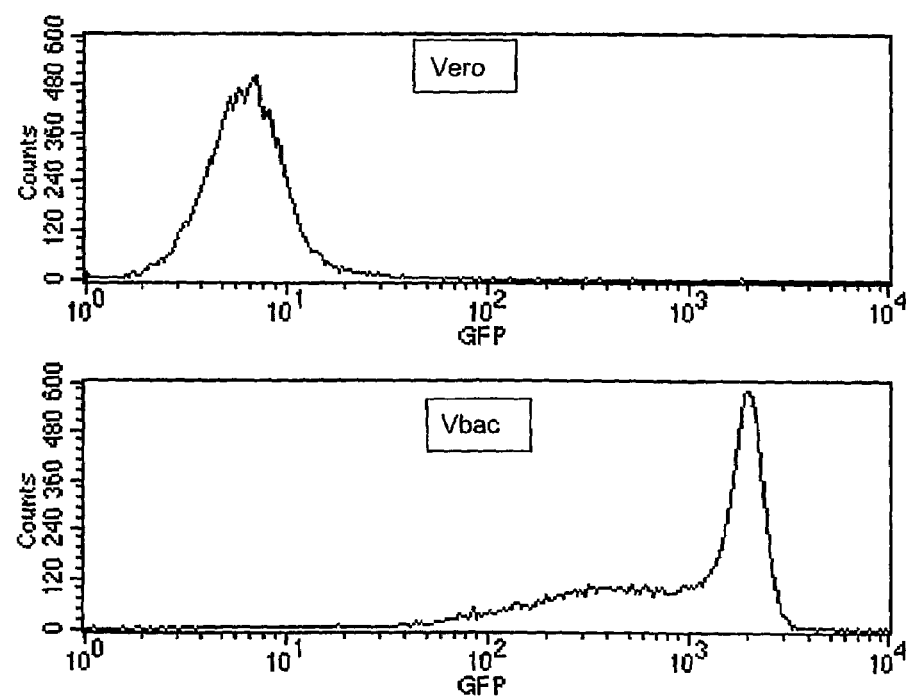

FIG. 10B shows the flow cytometry analysis of GP$^{64/F}$ surface expression in Vero and Vbac (pass 8) cells. Vbac and Vero cells were detached from plates with EDTA, fixed, and incubated with anti-GP64 antibodies. Cells were then incubated with an alexa-488-conjugated secondary antibody, and examined with flow cytometry.

Figure 11A:
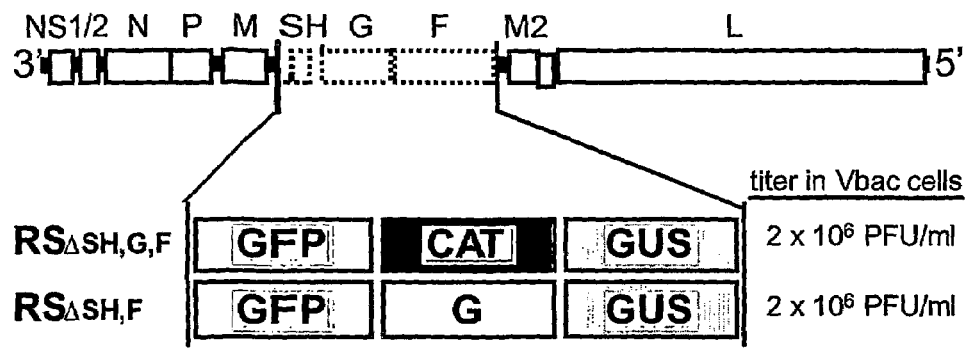

FIG. 11A is a schematic illustration of two engineered HRSVs. From a cDNA of the wild-type HRSV A2 strain, two cDNAs were constructed with altered glycoprotein gene content. In construct $RS_{\Delta SH,G,F}$, all three HRSV transmembrane glycoprotein ORFs (SH, G, and F) were deleted and replaced with those of GFP, CAT, and GUS, respectively. Construct $RS_{\Delta SH,F}$ is similar to $RS_{\Delta SH,G,F}$, however the HRSV G protein ORF was re-inserted in its native position.

Figure 11B:
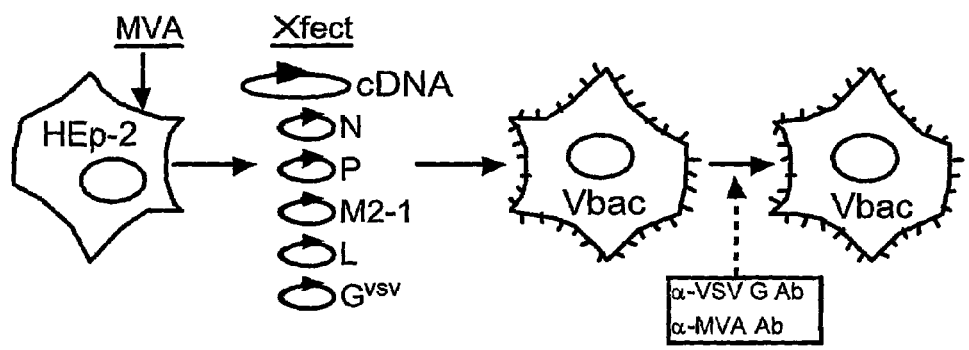

FIG. 11B depicts the recovery protocol for the engineered HRSVS. infectious HRSVs were recovered from cDNAs. A plasmid encoding a chimeric VSIV G protein (G$^{vsv}$) was included in the transfection of HEp-2 cells, and amplification of recovered viruses was done in Vbac cells. Pass 2 viruses were incubated with anti-VSIV G and anti-vaccinia antibodies before being used for the generation of pass 3 virus stocks. Pass 3 stocks were titrated in Vbac cells, yielding titers of 2×10$^6$ PFU/ml.

Figure 12:
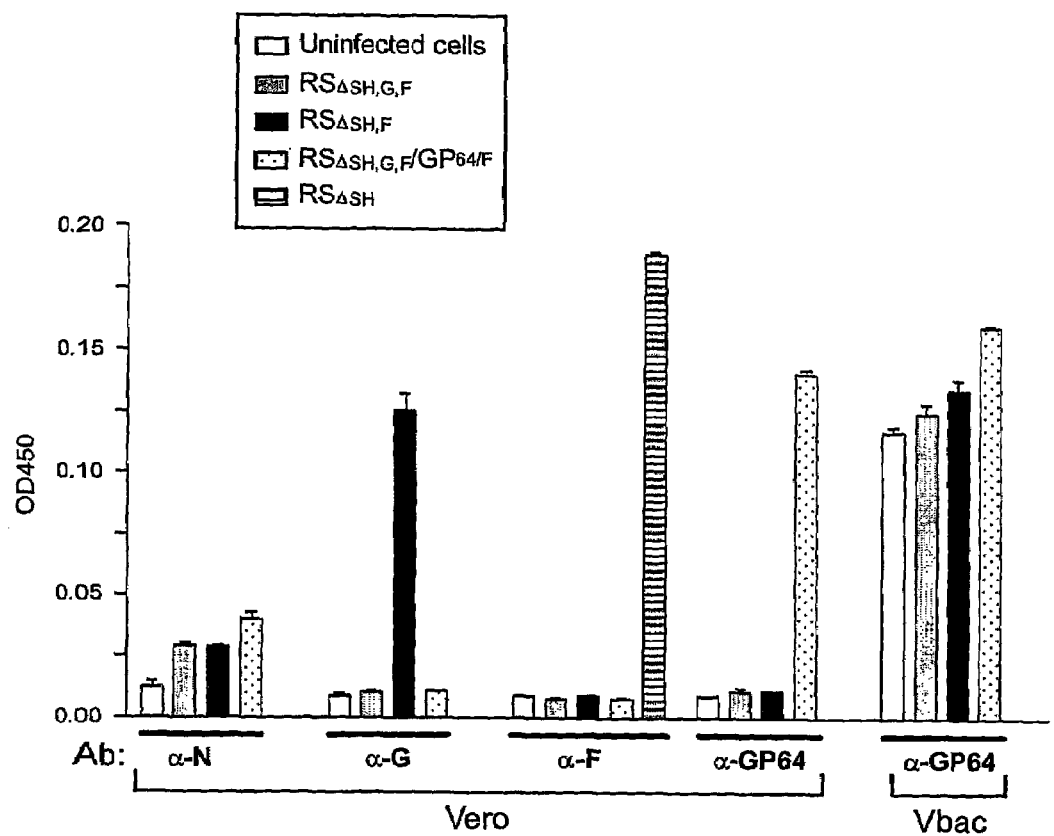

FIG. 12 shows the transmembrane glycoprotein expression by the engineered HRSVs. Protein expression in Vero and Vbac cells infected with the engineered viruses was examined at 28 h postinfection with CELISA. As a general comparison, Vero cells infected with virus $RS_{\Delta SH,G,F}$/GP$^{64/F}$ were included. As a positive control for F expression, Vero cells infected with $RS_{\Delta SH}$ was also included. α-N, anti-HRSV nucleocapsid protein antibody; α-G, anti-BRSV G antibody; α-F, anti-HRSV F antibody; and α-GP64, anti-GP64 antibody.

Figure 13:
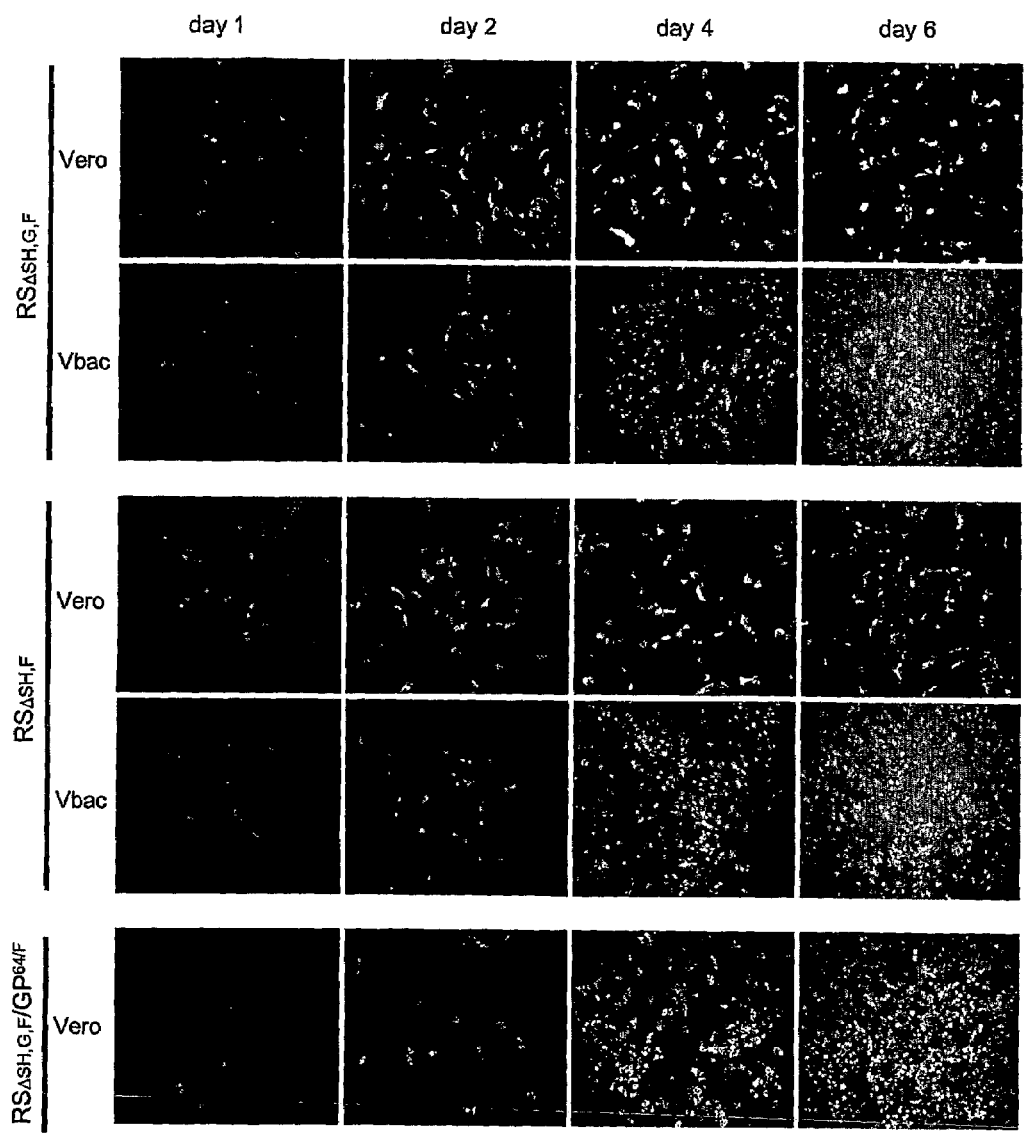

FIG. 13 demonstrates virus transmission in cell cultures. Vero and Vbac cells were plated at about 60% confluency, infected with viruses $RS_{\Delta SH,G,F}$ and $RS_{\Delta SH,F}$ at a multiplicity of 0.05, and incubated at 33° C. At day 1, 2, 4, and 6 postinfection, cells were fixed with 4% paraformaldehyde, and examined for GFP expression with fluorescence microscopy (magnification 200×). As a comparison, Vero cells infected with virus $RS_{\Delta SH,G,F}$/GP$^{64/F}$ were included.

Figure 14A:
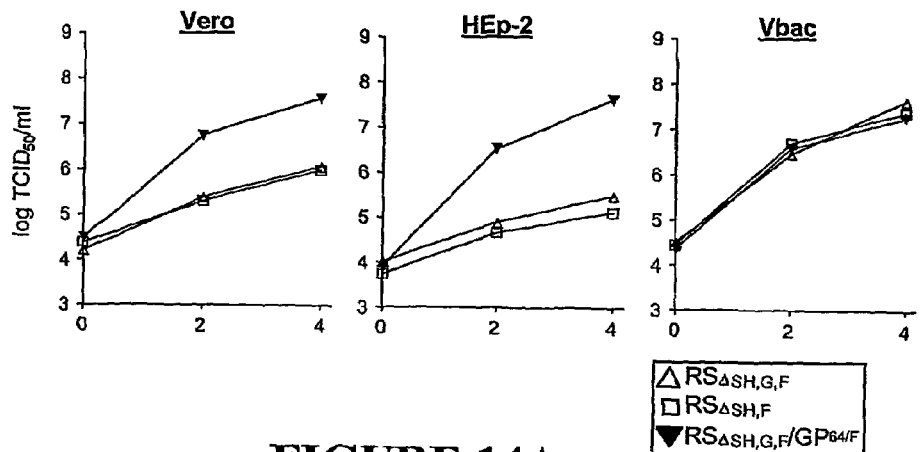

FIG. 14A illustrates the growth curves for engineered viruses in cell cultures. Vbac, Vero, and HEp-2 cells were infected with viruses $RS_{\Delta SH,G,F}$, $RS_{\Delta SH,F}$, or $RS_{\Delta SH,G,F}$/GP$^{64/F}$ at a multiplicity of 0.25, and incubated at 33° C. Immediately after infection (day 0) and at day 2 and 4 postinfection, cells were scraped into the supernatant and virus titers determined by $TCID_{50}$.

Figure 14B:
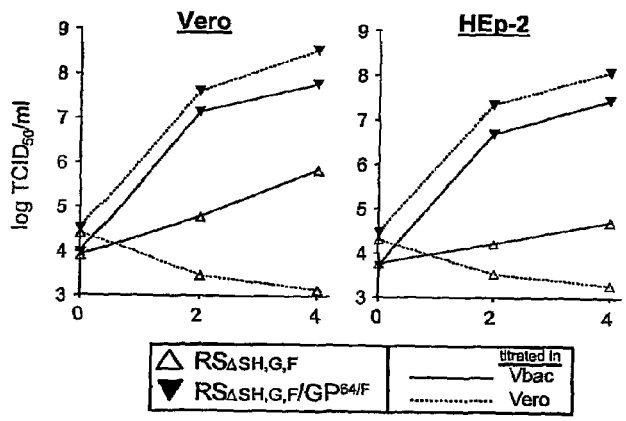

FIG. 14B indicates titration of the engineered virus in cell cultures. Frozen samples of viruses $RS_{\Delta SH,G,F}$ and $RS_{\Delta SH,G,F}$/GP$^{64/F}$ isolated from Vero and HEp-2 cells at day 0, 2, and 4 postinfection were titrated on Vero and Vbac cells by $TCID_{50}$.

Figure 14C:
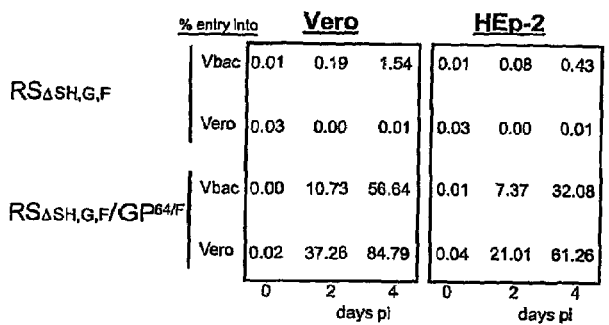

FIG. 14C compares the percentage of entry of engineered viruses by using flow cytometry. Frozen samples of viruses $RS_{\Delta SH,G,F}$ and $RS_{\Delta SH,G,F}$/GP$^{64/F}$ isolated from Vero and HEp-2 cells at day 0, 2, and 4 postinfection were diluted 10 times and used to infect Vero and Vbac cells. Viral entry was measured by counting GFP-expressing cells at 19 h postinfection.

Figure 15:
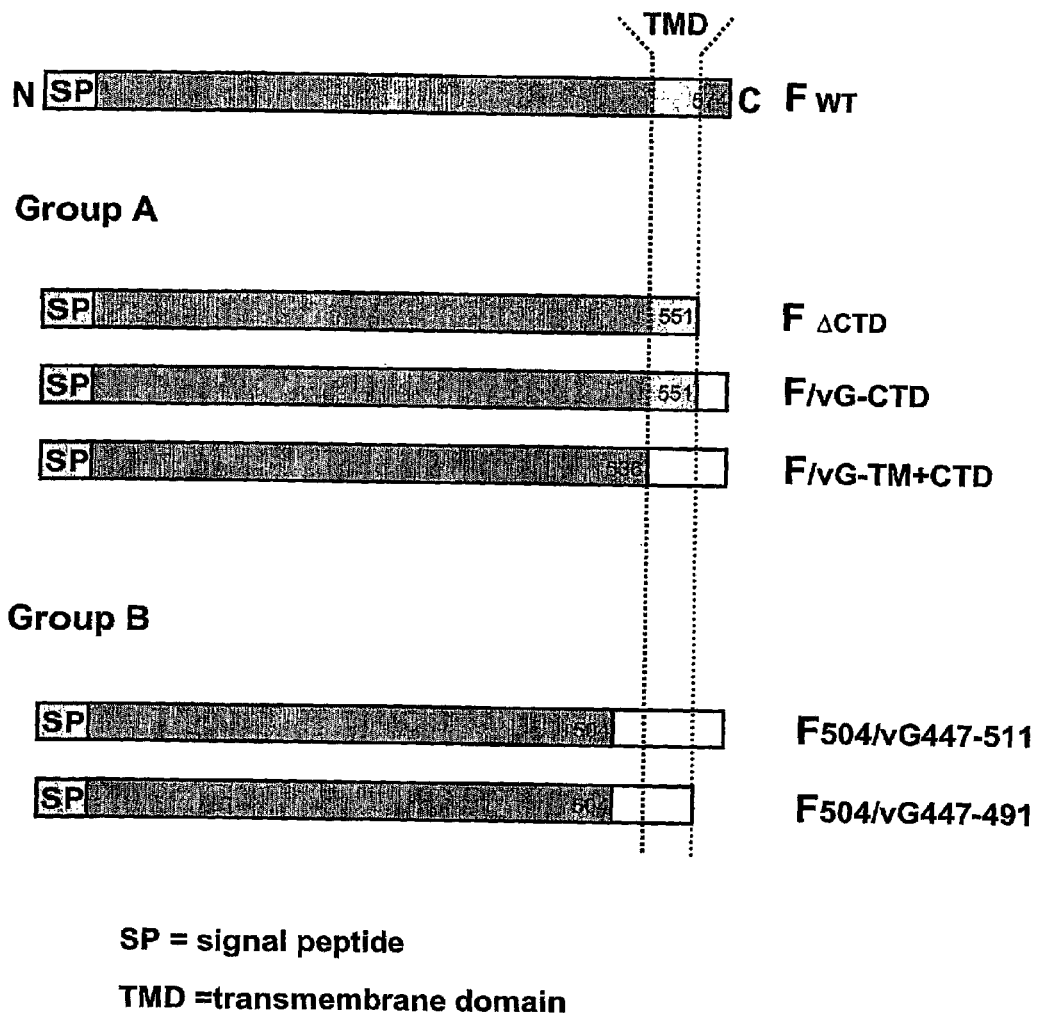

FIG. 15 schematically illustrates wild-type and genetically engineered HRSV F proteins.

Figure 16:
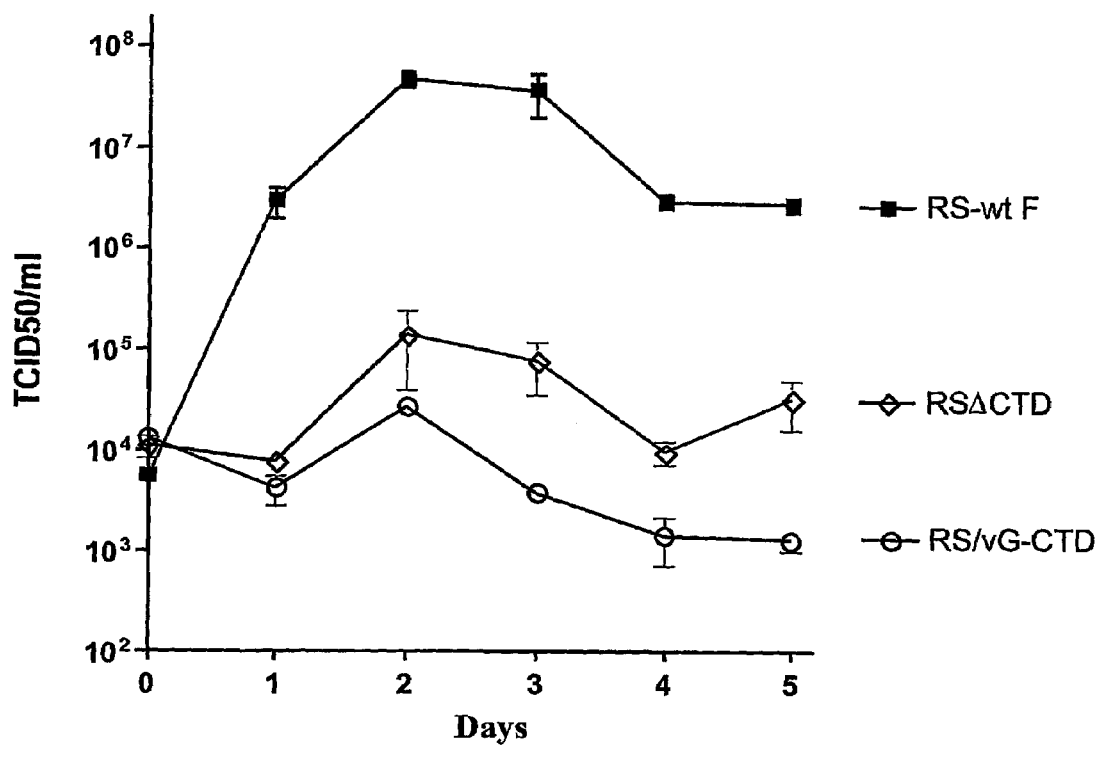

FIG. 16 shows the growth curves of wild-type and modified HRSVs in HEp-2 cells.

DETAILED DESCRIPTION OF THE INVENTION

The invention provides recombinant viruses comprising heterologous envelope proteins which are capable of mediating entry of the recombinant viruses into mammalian cells. In many embodiments, the heterologous envelope proteins confer improved stability of infectivity on the recombinant viruses, and enable production of high levels of infectious viruses. In some other embodiments, the heterologous envelope proteins impart temperature sensitivity to the recombinant viruses, and the recombinant viruses may be infectious but incapable of spreading between host cells. These advantages make the recombinant viruses supreme candidates for vaccine or gene therapy related applications.

Other recombinant viruses comprising heterologous envelope proteins can be found in U.S. patent application Ser. No. 10/262,238, filed Oct. 1, 2002, which claims priority from U.S. Provisional Patent Application Ser. No. 60/397,289, filed Jul. 19, 2002, and U.S. Provisional Patent Application Ser. No. 60/326,259, filed Oct. 1, 2001. The present application incorporates by reference the entire disclosure of U.S. patent application Ser. No. 10/262,238.

The heterologous envelope proteins suitable for the present invention include, but are not limited to, transmembrane proteins derived from baculovirus envelope proteins, such as GP64 or the functional equivalents thereof. Envelope proteins of other viruses (such as orthomyxoviruses including Thogoto or Dhori viruses) can also be used in the present invention, provided that these proteins are capable of imparting enhanced stability of infectivity to the recombinant viruses. As used herein, the term "heterologous protein" refers to a protein or polypeptide that does not naturally occur in the virus. An engineered variant of an endogenous protein is not considered a heterologous protein. The terms "endogenous protein" or "homologous protein" refer to a protein or polypeptide that is native or naturally occurring in the virus.

The viruses that can be modified by the invention include those that are sensitive to freezing/thawing or unstable when stored at or above 0° C. (e.g., at 4° C., room temperature, or 37° C.). These viruses can be either DNA or RNA viruses. Preferably, these viruses are pathogens for humans or animals. Exemplary viruses amenable to the present invention include, but are not limited to, those selected from *Paramyxoviridae* (e.g., pneumovirus, morbillivirus, or rubulavirus), *Arenaviridae* (e.g., arenavirus such as lymphocytic choriomeningitis virus), *Bunyaviridae* (e.g., phlebovirus or hantavirus), *Coronaviridae* (e.g., coronavirus or torovirus), *Filoviridae* (e.g., Ebola-like viruses), *Flaviviridae* (e.g., hepacivirus or flavivirus), *Herpesviridae* (e.g., simplexvirus, varicellovirus, cytomegalovirus, roseolovirus, or lymphocryptovirus), *Orthomyxoviridae* (e.g., influenza A virus, influenza B virus, influenza C virus, or thogotovirus), *Poxviridae* (e.g., orthopoxvirus, avipoxvirus, or leporipoxvirus), *Retroviridae* (e.g., lentivirus or spumavirus), *Rhabdoviridae* (e.g., lyssavirus, novirhabdovirus, or vesiculovirus), and *Togaviridae* (e.g., alphavirus or bubivirus). Other enveloped viruses or viruses with a membrane derived from the host cell plasma membrane can be also be modified according to the invention.

In many embodiments, the recombinant virus of the invention has improved stability of infectivity as compared to its wild-type counterpart, such as the wild-type virus from which the recombinant virus is derived. Stability of infectivity can be determined by monitoring the titer of a virus stock of interest. Numerous methods are available for determining virus titers. These methods are typically based on counting the total number of cells, or colonies of cells, that are infected by a specified fraction or dilution of the virus stock. Therefore, infectivity can be assessed by plaque forming units (PFU), 50% tissue culture infective dose ($TCID_{50}$), or other like measures, as appreciated by those skilled in the art. An exemplary method for titration of virus stocks is provided by Example 5 of this disclosure.

In one embodiment, the infectivity of the recombinant virus declines at a significantly slower rate than that of the corresponding wild-type virus. By "significantly slower," it means that the time for 50% infectivity reduction for the recombinant virus is at least 50% longer than that of the corresponding wild-type virus. For instance, the time for 50% infectivity reduction for the recombinant virus can be at least 1, 2, 3, 4, 5, 10, 20, 50, 100, 200, or more times longer than that for the corresponding wild-type virus. The time of harvest of the respective virus can be used as the starting point for calculating the 50% infectivity reduction time.

In another embodiment, the recombinant virus can be stored at above 0° C. for a substantial period of time without significantly losing infectivity. For instance, the recombinant virus can be stored at 4° C., room temperature (about 18-23° C., such as 22° C.), or 37° C. for at least 1 hour, 5 hours, 10 hours, 1 day, 2 days, 3 days, 4 days, 5 days, 6 days, 1 week, 2 weeks, 3 weeks, 4 weeks, 1 month, 2 months, or longer, and still retain at least 50%, 60%, 70%, 80%, 90%, 95%, or more of the original infectivity measured at the time of harvest. In contrast, under the same storage conditions, the corresponding wild-type virus may lose at least 50%, 60%, 70%, 80%, 90%, 95%, or more of the original infectivity. Because the reduction of infectivity depends on factors such as the original titer or concentration of the virus stock, the storage medium, the temperature range, the physical form of the virus stock (e.g., a lyophilized form versus a solution form), and the type of host cells, these factor should be kept similar or comparable for both the recombinant virus and the corresponding wild-type virus when their infectivities are compared.

In yet another embodiment, the recombinant virus is prepared from a paramyxovirus (e.g., a parainfluenza virus type I, II, or m, a respiratory syncytial virus, a measles virus, or a mumps virus) by incorporating a heterologous envelope protein into the viral membrane. The heterologous envelope protein comprises the ectodomain of a baculovirus GP64 protein, and is capable of mediating entry of the recombinant paramyxovirus into mammalian host cells.

GP64 is a type I integral membrane protein which bears a signal peptide at the N-terminus and a transmembrane domain near the C-terminus. The ectodomain of GP64 includes hydrophobic regions involved in membrane fusion and protein oligomerization. In Autographa californica multicapsid nucleopolyhedrovirus (AcMNPV), GP64 is involved in both receptor binding and membrane fusion during viral entry. In particular, GP64 can mediate low pH triggered membrane fusion during entry by endocytosis. GP64 are also required for viral assembly and efficient production of budded virions during viral exit.

GP64 protein is highly conserved among a number of baculoviruses, such as AcMNPV, Orgyia pseudotsugata multinucleocapsid nuclear polyhedrosisvirus (OPMNPV), and Choristoneura fumiferana multiple nuclear polyhedrosisvirus (CfMNPV). These baculoviruses are relatively closely related. Several more distantly related baculoviruses possess an envelope protein that serves as a functional equivalent of GP64. Examples of these functional equivalents of GP64 include, but are not limited to, the Spodoptera exigua multicapsid nucleopolyhedrovirus Se8 protein and the Lymantria dispar multicapsid nucleopolyhedrovirus Ldl30 protein. In addition, several orthomyxoviruses contain an envelope protein, GP75, which is phylogenetically related to the baculovirus GP64 protein. All of these envelope proteins can be employed in the present invention to make recombinant viruses.

The amino acid sequences of baculovirus GP64 proteins that are amenable to the present invention can be readily obtainable from Entrez or other publicly accessible sequence databases. The Entrez accession numbers for GP64 proteins include, but are not limited to, NP_054158 (Autographa californica nucleopolyhedrovirus), NP_046282 (Orgyia pseudotsugata multicapsid nucleopolyhedrovirus), NP_848430 (Choristoneura fumiferana multicapsid nucleopolyhedrovirus), AAF09194 (Hyphantria cunea nucleopolyhedrovirus), and $NP_{13}$ 203281 (Epiphyas postvittana nucleopolyhedrovirus). As used herein, GP64 protein includes not only naturally occurring GP64 proteins, but also the biologically active variants thereof. A "variant" is a polypeptide that differs from the original GP64 protein by one or more amino acid substitutions, deletions, insertions, and/or other modifications. These modifications do not significantly reduce the biological activity of the original GP64 protein (i.e., the activity to mediate entry of the recombinant virus into a mammalian cell). By "not significantly reduce," it means that the biological activity of a variant is at least 10% of that of the original GP64 protein. For instance, the biological activity of a variant can be at least 20%, 30%, 40%, 50%, 60%, 70%, 80%, 90%, 95%, or 100% of that of the original GP64 protein. The biological activity of a variant can also be higher than that of the original GP64 protein. The activity to mediate viral entry into mammalian cells can be determined using any suitable method known in the art. Exemplary viral entry and membrane attachment/fusion assays are described in the Examples of this disclosure.

The amino acid sequence of a variant is substantially identical to that of the original GP64 protein. A variant typically shares at least 70%, 80%, 85%, 90%, 95%, 99%, or more global sequence identity or similarity with the original polypeptide. Sequence identity or similarity can be determined using various methods known in the art, such as Basic Local Alignment Tool (BLAST) described in Altschul, et al., J. MOL. BIOL., 215:403-410 (1990), the algorithm of Needleman, et al., J. MOL. BIOL., 48:444-453 (1970), the algorithm of Meyers, et al., COMPUT. APPL. Biosci., 4:11-17(1988), dot matrix analysis, and the dynamic programming method. In one embodiment, the sequence identity or similarity is determined by using the Genetics Computer Group (GCG) programs GAP (Needleman-Wunsch algorithm). Default values assigned by the programs are employed (e.g., the penalty for opening a gap in one of the sequences is 11 and for extending the gap is 8). Similar amino acids can be defined using the BLOSUM62 substitution matrix. The original polypeptide and its variant can be substantially identical in one or more regions, but divergent in others.

A variant can be prepared by deletion or addition of amino acid residues. For instance, 1, 2, 3, 4, 5, 10, 15, 20 or more amino acid residues can be deleted to added without significantly reducing the biological activity of the original GP64 protein. In one specific example, the added amino acid residues include an immunogenic epitope capable of eliciting an immunoprotective response in humans.

A variant can also be prepared by making one or more conservative substitutions. A conservative substitution is one in which the original amino acid and its substitute have similar properties such that the biological activity of the substituted polypeptide is not significantly changed. Conservative amino acid substitutions can be made on the basis of similarity in polarity, charge, solubility, hydrophobicity, hydrophilicity, or the amphipathic nature of the residues. For instance, conservative amino acid substitutions can be made among amino acids with basic side chains, such as lysine (Lys or K), arginine (Am or R) and histidine (His or H); amino acids with acidic side chains, such as aspartic acid (Asp or D) and glutamic acid (Glu or E): amino acids with uncharged polar side chains, such as asparagine (Asn or N), glutamine (Gln or Q), serine (Ser or S), threonine (Thr or T), and tyrosine (Tyr or Y); and amino acids with nonpolar side chains, such as alanine (Ala or A), glycine (Gly or G), valine (Val or V), leucine (Leu or L), isoleucine (Ile or I), proline (Pro or P), phenylalanine (Phe or F), methionine (Met or M), tryptophan (Trp or W) and cysteine (Cys or C).

In addition, a variant can be prepared by making one or more non-conservative substitutions. The non-conservative substitution(s) preferably does not significantly reduce the biological activity of the original GP64 protein.

In one specific example, a variant includes 1, 2, 3, 4, 5, 10, 15, 20, or more amino acid substitutes in the original sequence. The substitutions(s) can be conservative, non-conservative, or both. In another specific example, a variant includes one or more naturally-occurring mutations, such as allelic variations or polymorphisms.

In another embodiment, the heterologous envelope protein is a full-length naturally occurring GP64 protein or a variant thereof. In still another embodiment, the heterologous envelope protein comprises the ectodomain and the transmembrane domain of a GP64 protein and the cytoplasmic tail domain (or a fragment thereof) of an endogenous transmembrane protein. In many cases, the cytoplasmic tail domains of endogenous envelope proteins play important roles in membrane fusion, glycoprotein incorporation, budding, or morphology. Thus, by employing at least a portion of the cytoplasmic tail domain of an endogenous envelopment protein, the assembly and infectivity of the recombinant virus can be optimized.

The heterologous envelope protein can be incorporated into the membrane of the recombinant virus by using any suitable method known in the art. In one embodiment, the coding sequence of the heterologous envelope protein is inserted into the genome of a paramyxovirus. Expression of the modified genome produces the heterologous envelope protein, which in tuan is assembled into the viral particle. In another embodiment, the coding sequence of the heterologous envelope protein is introduced into the genome of the paramyxovirus by substituting one or more genes that encode endogenous transmembrane protein(s).

In yet another embodiment, the heterologous envelope protein is incorporated into the recombinant paramyxovirus by using a transcomplementing packaging system. The system typically involves the use of a packaging cell line which is transiently, or preferably, stably transfected with an expression vector encoding the heterologous envelope protein. The system also includes a paramyxovirus cDNA which may comprise deletions of the coding sequence(s) for one or more endogenous transmembrane proteins from the viral genome. In one specific example, all of the endogenous transmembrane protein coding sequences are deleted from the viral genome. As a result, expression from the paramyxovirus cDNA is not sufficient for producing an infectious viral particle. By co-expressing the cDNA in the packaging cell line, however, the heterologous envelope protein complements the absence of the endogenous transmembrane protein(s), thereby allowing the assembly of an infectious paramyxoviral particle.

Virions carrying a heterologous envelope protein are referred to as "pseudotyped" viruses. Pseudotyped virions can be used for applications such as gene therapies or preparation of vaccines. Pseudotyped virions can also be employed as valuable tools for dissecting the functions necessary for assembly of mature virions or budding at the cell surface.

In yet another embodiment, the recombinant virus is a recombinant human respiratory syncytial virus (HRSV) which includes a heterologous envelope protein comprising the ectodomain of a baculovirus GP64 protein. As demonstrated by the Examples of this disclosure, recombinant HRSVs with GP64-based envelope proteins can have improved membrane fusion activities and enhanced growth rates at 33° C., as compared to 37° C. Accordingly, the GP64-based envelope protein can render the recombinant HRSV temperature sensitive with restricted replication at 37° C. This feature can attenuate the recombinant virus, when used as a vaccine, for replication in the lower respiratory tract where the virus may cause diseases, and restrict the virus to replication in the cooler upper respiratory tract where the virus may replicate and stimulate an immune response.

The temperature sensitivity imparted by GP64-based envelope proteins is different from that possessed by other known live attenuated viruses. These previously known, temperature sensitive viruses typically include mutations generated by either chemical mutagenesis or cold adaptation. Cold adaptation is a process by which virus is adapted to growth at temperatures colder than those at which it normally optimally grows. The temperature sensitivity conferred by these genetic modifications, however, is frequently reversible, creating safety concerns when these viruses are used as vaccines or therapeutic vectors. In contrast, the temperature sensitivity provided by the GP64-based envelope protein seems to be inherently associated with the structure of the protein. Loss of the temperature sensitivity is often coupled with loss of the function of the GP64-based protein, which renders the recombinant virus noninfectious to host cells.

The GP64-based envelope protein can also confer stability of infectivity on the recombinant HRSV. In one embodiment, the recombinant virus stock can be stored under specified storage conditions for at least 1 day, 2 days, 3 days, 4 days, 5 days, 6 days, 1 week, 2 weeks, 3 weeks, 4 weeks, 1 month, 2 month, or longer, while retaining at least 30%, 40%, 50%, 60%, 70%, 80%, 90%, 95%, or more of the original activity measured at the time of harvest. In comparison, a wild-type HRSV from which the recombinant HRSV can be derived may lose at least 30%, 40%, 50%, 60%, 70%, 80%, 90%, 95%, or more of the original activity measured at the time of harvest.

In addition, the GP64-based envelope protein may allow production of high-titer virus stocks. In one embodiment, the recombinant HRSV has a titer of at least $10^6$, $10^7$, $10^8$, or more PFU/ml. In another embodiment, the recombinant HRSV has a titer of at least $10^6$, $10^7$, $10^8$, or more $TCID_{50}$/ml. $TCID_{50}$ can be determined using the procedure described in Example 5 of this disclosure.

Various methods are available for incorporating the GP64-based envelope protein into the recombinant virus. For instance, the GP64-based envelope protein can be introduced into the recombinant virus by replacing an endogenous transmembrane protein coding sequence, such as the SH, G or F gene, with the coding sequence of the GP64-based envelope protein. The recombinant virus thus prepared can retain both infectivity and transmissibility.

For another instance, the GP64-based envelope protein can be introduced into the recombinant virus by using a transcomplementing packaging system. A packaging cell line transiently or stably transfected with the coding sequence of the GP64-based envelope protein can be used to provide the GP64-based envelope protein in trans to complement the HRSV viral cDNA which lacks one or more functional endogenous transmembrane protein genes. The recombinant virus thus obtained is not transmissible, but can be infectious due to the presence of the GP64-based envelope protein. The non-transmissibility of this recombinant HRSV provides further safety and attenuation in that the virus can only enter, replicate, and express its encoded antigens in the first cell it infects and cannot spread to other cells. This feature represents a major advantage over other known attenuated HRSVs.

Figure 1:
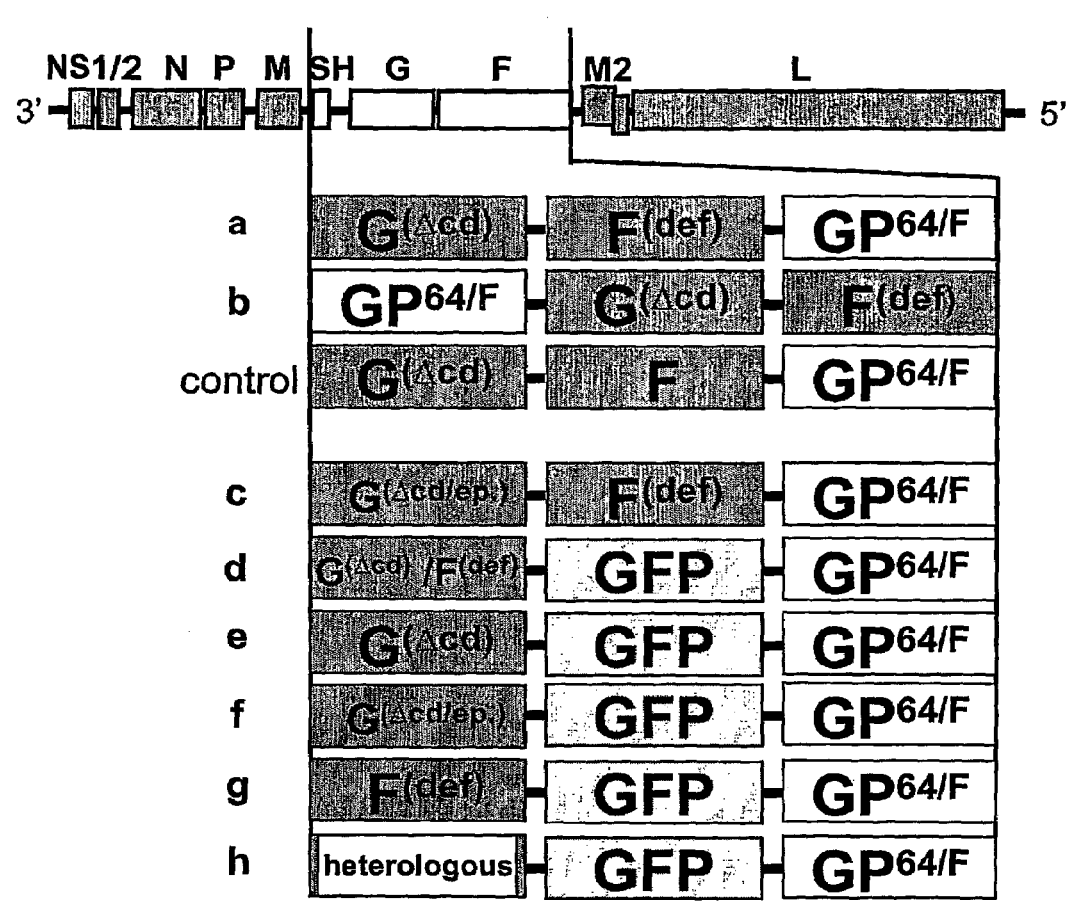

Examples of transmissible recombinant HRSV are illustrated in FIG. 1. In vector a, the SH, G, and F genes of a wild-type HRSV are replaced by the coding sequences of $G^{(\Delta cd)}$, $F^{(def)}$, and $GP^{64/F}$, respectively. $G^{(\Delta cd)}$ denotes a modified SV G protein with the central conserved domain deleted. The central conserved domain of G (amino acid residues 164-176) may be involved in enhanced pathogenesis observed during a 1960's vaccination attempt. This domain can be deleted without loss of G function. $F^{(def)}$ presents a defective (non-functional) HRSV F protein. A variety of point mutation or deletions can be applied to interfere with F function while maintaining the native F conformation. These mutations or deletions can be introduced, for example, into the maturation cleavage sites or the fusion domain. $GP^{64/F}$ is described in Example 2 of this disclosure. The modified G and F genes are moved forward in the genome of vector a to enhance their respective expression levels. This is because the level of transcription of a HRSV gene can be determined by the location of the gene in the genome relative to the single 3' transcriptional promoter. As appreciated by those of ordinary skill in the art, the modified G and F genes can also be placed at other positions or in other orders without significantly altering the property of the recombinant virus. In vector b, the SH, G, and F genes of the wild-type HRSV are replaced by the coding sequences of $GP^{64/F}$, $G^{(\Delta cd)}$, and $F^{(def)}$, respectively.

In vector c, the SH, G, and F genes are replaced by the coding sequences of $G^{(\Delta cd/ep)}$, $F^{(def)}$, and $GP^{64/F}$, respectively. $G^{(\Delta cd/ep)}$ denotes a $G^{(\Delta cd)}$ containing at least one epitope. It has been shown that the G protein can be extensively modified without interference in G processing or function. Particularly, the ectodomain of the G protein is substantial flexible and can accommodate numerous alterations. Immunoprotective epitopes from homologous (e.g., F protein) or heterologous sources (e.g., influenza or parainfluenza I, II, or E) can be introduced into the G protein to make the recombinant HRSV a potential multiple-component vaccine. The epitope(s) can be either inserted within the ectodomain domain or fused to the C-terminus of the G-protein for display at the viral membrane.

In vector d, the SH, G, and F genes are replaced by the coding sequences of $G^{(\Delta cd/ep)}/F^{(def)}$, GFP, and $GP^{64/F}$, respectively. $G^{(\Delta cd/ep)}/F^{(def)}$ represents a fusion protein between $G^{(\Delta cd)}$ and $F^{(def)}$. A soluble F/G fusion protein (amino acid residues 1-489 of the protein F plus amino acid residues 97-297 of the G protein) can confer protection against HRSV challenge in animal models. GFP refers to green fluorescent protein, which is included as a marker or placekeeper gene. See also Example 4 of this disclosure. In vector h, the SH gene is replaced by a "heterologous gene" which can encode any protein, protein domain, or epitope of interest. The heterologous gene can also be introduced at the position of the F or G gene, or inserted at other places in the HRSV genome.

Figure 2:
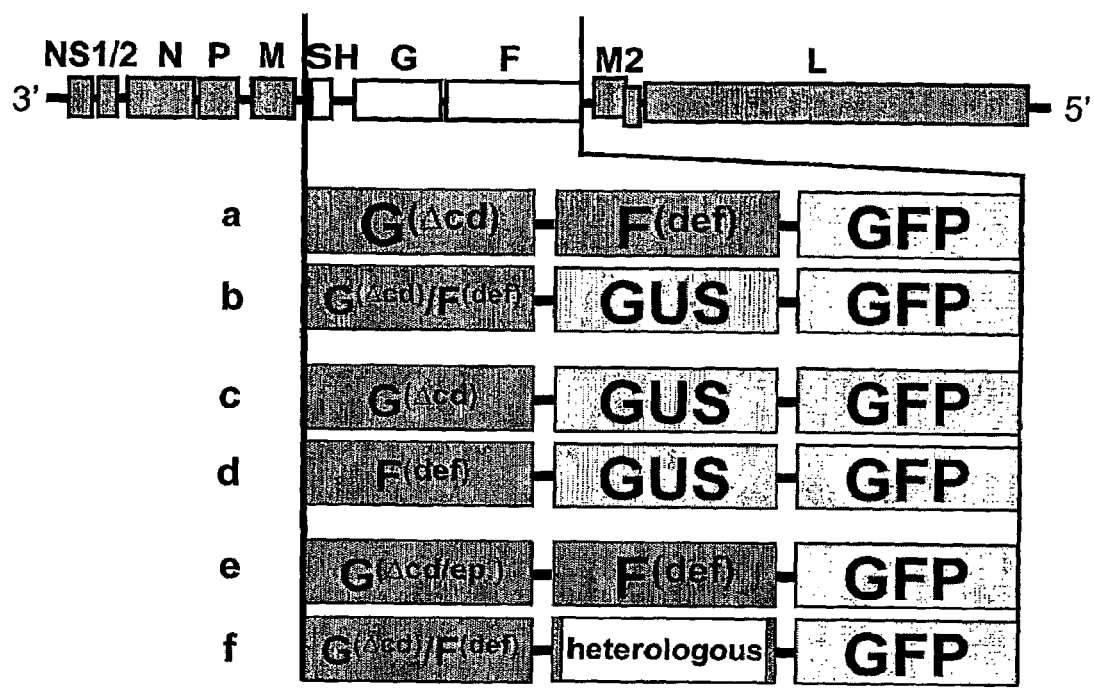
FIG. 2 schematically depicts the genomes of non-spreading recombinant HRSVs.

FIG. 2 schematically depicts the genomes of exemplary recombinant HRSVs which cannot spread but are infectious when complemented by a heterologous GP64-based envelope protein. GUS represents β-glucuronidase which, like GFP, is included as a marker or placekeeper gene. The non-spreading HRSVs preferably retain a modified G or F gene (e.g., $G^{(\Delta cd)}$ or $F^{(def)}$) for eliciting desirable immune responses against HRSVs. Although the central conserved domain is deleted from the recombinant viruses depicted in FIGS. 1 and 2, one of ordinary skill would appreciate that the complete G protein can also be used for preparing a recombinant virus of the present invention. In addition, genes encoding other heterologous proteins can be used to replace the GFP gene employed in the recombinant viruses depicted in FIGS. 1 and 2.

In another embodiment, the recombinant HRSV is infectious but can not replicate, transcribe, or translate in infected host cells. This can be achieved, for instance, by deleting respective DNA or RNA polymerases. The feature adds additional safety to the recombinant virus for use as a vaccine or a therapeutic vector (e.g., a gene therapy vector or a viral therapy vector).

As exemplified by vectors c, f, and h of FIG. 1 and vectors e and f of FIG. 2, the invention contemplates incorporation of homologous or heterologous epitopes into the recombinant viruses. Epitopes of any pathogen can be incorporated. Exemplary pathogens include, but are not limited to, viruses (e.g., picornavirus, coronavirus, togavirus, fiavirvirus, rhabdovirus, paramyxovirus, orthomyxovirus, bunyavirus, arenvirus, reovirus, retrovirus, papovavirus, parvoviuus, herpesvirus, poxvirus, hepadnavirus, and spongiform virus), bacteria (e.g., *Actinobacillosis lignieresi, Actinomyces bovis, Aerobacter aerogenes, Anaplasma marginale, Bacillus anthracis, Borrelia anserina, Brucella canis, Clostridium chauvoei, C. hemolyticium C. novyi, C perfringens, C. septicum, C. tetani, Corynebacterium equi, C. pyogenes, C. renale, Cowdria ruminantium, Dermatophilus congolensis, Erysipelothrix insidiosa, Escherichia coli, Fusiformis necrophorus, Haemobartonella canis, Hemophilus* spp. *H. suis, Leptospira* spp., *Moraxella bovis, Mycoplasma* spp. *M. hyopneumoniae, Nanophyetus salmincola, Pasteurella anatipestifer, P. hemolytica, P. multocida, Salmonella abortus-ovis, Shigella equirulis, Staphylococcus aureus, S. hyicus. S. hyos, Streptococcus agalactiae, S. dysgalactiae, S. equi, S. uberis, Vibrio fetus, Corynebacterium diptheriae, Mycobacterium bovis, M. leprae, M. tuberculosis, Nocardia asteroides, Clostridium botulinum, C. difficile, C. perfringens, Streptococcus pneumoniae, S. pyogenes, Bordetella pertusiss, Psudomonas aeruginos, Campylobacter jejuni, Brucella* spp., *Francisella tularenssis, Legionella pneumophila, Chlamydia psittaci. C. trachomatis, Klebsiella pneumoniae, Salmonella typhi, S. typhimurium, Yersinia enterocolitica, Y. pestis, Vibrio cholerae, Haemophilus influenza, Mycoplasma pneumoniae, Neiseseria gonorrhoeae, N. meninigitidis, Coxiella burneti, Rickettsia mooseria, R. prowazekii, R. rickettsii, R. tsutsugamushi, Borrelia* spp., *Leptospira interrogans, Treponema pallidum*, and *Listeria monocytogenes*), protozoa (e.g., the coccidiosis-causing *Eimeria* species, *Anaplasma marginale, Giardia* species, *Babesia* species, *Trichomonas foetus, Entamoeba histolytica, Balantidium coli; Plasmodium* species, *Leishmania* species, *Trypanosoma* species, *Entamoeba histolytica, Trichomonas vaginalis, Toxoplasmosa gondii*, and *Pneumocystis carinii*), fungi (e.g., ringworms and *Blastomyces dermatitidis*), parasites (e.g., trypanosomes, tapeworms, roundworms, and helminthes), and other infectious or pathogenic microbes.

Preferred viral targets include, but are not limited to, human immunodeficiency virus, human respiratory syncytial virus, influenza, herpes simplex virus 1 and 2, measles virus, hepatitis A virus, hepatitis B virus, hepatitis C virus, smallpox virus, polio virus, west Nile virus, coronavirus associated with severe acute respiratory syndrome, rotavirus, papilloma virus, papillomaviruses, Epstein-Barr virus, human T-cell lymphotropic virus type I, and Kaposi's sarcoma-associated herpesvirus.

Multiple immunogenic epitopes can be introduced into the same recombinant virus. These epitopes can be incorporated into the membrane, capsid, or other portions of the recombinant virus. Alternatively, the coding sequences for the epitopes can be inserted into the genome of the recombinant virus. Expression of the viral genome produces the epitopes, which in turn are presented to the immune system for triggering desirable immune responses.

The invention further contemplates pharmaceutical compositions comprising the recombinant virus of the invention. These pharmaceutical compositions can be used as vaccines to induce immune responses against the epitope(s) carried by the recombinant virus of invention. The elicited immune responses can be cell-mediated, humoral, or both.

Any standard method can be used to prepare the pharmaceutical composition of the invention. The pharmaceutical composition typically includes a pharmaceutically acceptable carrier. Exemplary pharmaceutically acceptable carriers include, but are not limited to, physiologically balanced culture medium, phosphate buffered saline solution, water, or emulsions, such as an oil/water emulsion, various types of wetting agents and protein stabilizers. Each carrier is "acceptable" in the sense of being compatible with the other ingredients of the formulation and not injurious to the patient. A pharmaceutical carrier can also include solubilizers, fillers, binders, absorbents, bases, buffering agents, lubricants, controlled release vehicles, diluents, emulsifying agents, humectants, lubricants, dispersion media, coatings, antibacterial or antifingal agents, isotonic and absorption delaying agents, and the like, that are compatible with pharmaceutical administration. The use of media and agents for pharmaceutically active substances is well-known in the art.

In one embodiment, the recombinant virus is maintained in a pharmaceutically acceptable carrier and stored at above 0° C. (e.g., 4° C., room temperature or 37° C.) before administration. In another embodiment, the recombinant virus is mixed with cryoprotective additives or stabilizers such as proteins (e.g., albumin, gelatin), sugars (e.g., sucrose, lactose, and sorbitol), amino acids (e.g., sodium glutamate), saline, or other protective agents. This mixture is then desiccated or lyophilized for transport and storage, and reconstituted prior to administration. Lyophilized virus can be maintained at about 4° C., and when ready for use, reconstituted in a stabilizing solution, with or without adjuvant. In yet another embodiment, the recombinant virus is inactivated and then mixed with an adjuvant, saline and a detergent such as phosphate Tween buffer. Other standard methods can also be used to prepare virus vaccines Immunogenicity can be significantly improved if the recombinant virus is co-administered with an immunostimulatory agent or adjuvant. Adjuvants enhance immunogenicity but are not necessarily immunogenic themselves. Immunostimulatory agents or adjuvants have been used for years to improve the host immune responses to vaccines.

Suitable adjuvants are well known to those skilled in the art and include, without limitation, aluminum phosphate, saponins complexed to membrane protein antigens to produce immune stimulating complexes (ISCOMS), plutonic polymers with mineral oil, killed mycobacteria in mineral oil, Freund's complete adjuvant, bacterial products, such as muramyl dipeptide (MDP) and lipopolysaccharide (LPS), as well as monophoryl lipid A, QS 21, and polyphosphazene, or components or derivatives thereof. Some of these adjuvants are toxic and may cause undesirable side-effects. Caution should be used for selecting proper adjuvants.

The vaccines can be administered in a manner compatible with the dosage formulation, and in such amount as will be therapeutically effective (e.g., immunogenic and protective). The quantity to be administered depends on the subject to be treated, including, for example, the capacity of the immune system of the individual to synthesize antibodies, and, if needed, to produce a cell-mediated immune response. Precise amounts of active ingredient required to be administered depend on the judgment of the practitioner and may be monitored on a patient-by-patient basis. However, suitable dosage ranges are readily determinable by one skilled in the art and generally range from about $10^2$ to about $10^9$ plaque forming units (PFU) or more of virus per patient, more commonly, from about $10^4$ to about $10^5$ PFU of virus per patient. The dosage may also depend, without limitation, on the route of administration, the patient's state of health and weight, and the nature of the formulation.

The pharmaceutical composition can be formulated to be compatible with its intended route of administration. Examples of routes of administration include oral, nasal, topical (including transdermal, buccal, and sublingual), parenteral (including subcutaneous), pulmonary, intravenous, intradermal, rectal, or transmucosal. More than one route of administration can be employed either simultaneously or sequentially (e.g., boosting). In one instance, the administration is carried out by using an implant.

In one specific example, live viral vaccines are administered intranasally, orally, parenterally, or applied to any mucosal surface (e.g., nasal, oral, eye, or rectal). In another specific example, inactivated whole virus vaccines are administered parenterally or to any mucosal surface.

Upon inoculation with the vaccine composition of the invention, the immune system of the host can respond to the vaccine by producing antibodies, both secretory and serum, specific for the epitope(s) included in or expressed by the recombinant viruses. As a result of the vaccination, the host can become partially or completely immune to infection by the pathogen(s) carrying the epitope(s). Where the epitope(s) is associated with HRSV, the host may become resistant to developing moderate or severe RSV infection, particularly of the lower respiratory tract.

As described above, the recombinant virus of the invention can carry or express multiple epitopes. These epitopes can be associated with pathogens of different kinds or species. They can also be associated with different stains of the same species. For instance, a recombinant RSV virus can carry epitopes of multiple stains of HRSV. In addition, due to the phenomenon of cross-protection among certain strains, immunization with one strain may protect against several different strains of the same species or subgroup. Furthermore, different recombinant viruses carrying different epitopes can be mixed together and administered simultaneously, separately, or sequentially.

In some cases, it may be desirable to combine the recombinant virus vaccine of the invention with other known vaccines which induce protective responses to other agents, particularly other childhood viruses. Moreover, the recombinant virus vaccine of the invention can be combined with components of selected viruses, such as isolated envelope or capsid proteins.

Single or multiple administrations of the vaccine composition of the invention can be carried out. In neonates and infants, multiple administration may be required to elicit sufficient levels of immunity. Administration can begin within the first month of life, and continue at intervals throughout childhood, such as at two months, six months, one year and two years, as necessary to maintain sufficient levels of protection against the pathogen of interest. Similarly, adults who are particularly susceptible to repeated or serious infection by the pathogen of interest, such as health care workers, day care workers, elderly and individuals with compromised cardiopulmonary function, may require multiple immunizations to establish and/or maintain protective immune responses. Levels of induced immunity can be monitored by measuring amounts of neutralizing secretory and serum antibodies, and dosages adjusted or vaccinations repeated as necessary to maintain desired levels of protection.

Preferably, the virus vaccine of the invention does not lead to immunopotentiation or exacerbated diseases. More preferably, the recombinant virus lacks transmissibility and is temperature sensitive. In such a case, a complementation cell line may be used to provide the necessary envelope protein to guide viral entry into host cells. Without the complementation cell line, the viral particle can infect but cannot spread.

The effectiveness of the vaccine composition of the invention can be evaluated by using in vitro or in vivo models. A variety of animal models of RSV infection have been described in Meignier, et aL, eds., ANIMAL MODELS OF RESPIRATORY SYNCYTIAL VIRUS INFECTION (Merieux Foundation Publication, 1991). A cotton rat model of RSV infection is also described in U.S. Pat. No. 4,800,078 and Prince, et aL, VIRUS RES., 3:193-206 (1985). The cotton rat model is believed to be predictive of attenuation and efficacy in humans. In addition, a primate model of RSV infection is described in Richardson, et al., J. MED. VIROL., 3:91-100 (1978) and Wright, et al., INFECT. IMMUN., 37:397-400 (1982).

The recombinant virus of the invention can be used in diagnostic applications. In one embodiment, a method useful for detecting the presence or absence of an antibody specifically reactive with an epitope is provided. The method includes the steps of contacting a sample with the recombinant virus carrying the epitope, and detecting any binding between an antibody component in the sample and the recombinant virus. Suitable binding assays for this purpose include, without limitation, ELISA (enzyme-linked immunosorbent assay), RIA (radioimmunoassay), and FACS (fluorescence-activated cell sorter).

Furthermore, the invention contemplates therapeutic vectors comprising the recombinant virus of the invention. The recombinant virus can include proteins capable of specifically targeting the virus to desired cells or tissues. For instance, a ligands or a receptor for a specific cell surface marker can be fused or conjugated to the envelope of the recombinant virus. The ligand or receptor can direct the virus to bind to the cells that carry the specific cell surface marker. In one specific example, the ligand or receptor is a protein domain fused to or within the ectodomain of a baculovirus GP-64 protein or an endogenous transmembrane protein of the recombinant virus. Therapeutic gene or genes can be inserted into the genome of the recombinant virus using any conventional methods known in the art.

It should be understood that the above-described embodiments and the following examples are given by way of illustration, not limitation. Various changes and modifications within the scope of the invention will become apparent to those skilled in the art from the present description.

EXAMPLES

Example 1

Cells and Antibodies

Vero 76 (ATCC No. CRL-1587, hereinafter referred to as Vero) and HEp-2 (ATCC No. CCL-23) cells were acquired from the American Type Culture Collection (ATCC), and grown in standard growth medium. In one specific example, Vero cells are grown in a medium containing (1) Dulbecco's modified Eagle's medium with 4 mM L-glutamine adjusted to contain 1.5 g/L sodium bicarbonate and 4.5 g/L glucose (97%) and (2) fetal bovine serum (3%). In another specific example, HEp-2 cells are grown in a medium containing (1) Minimum essential medium (Eagle) with 2 mM L-glutamine and Earle's BSS adjusted to contain 1.5 g/L sodium bicarbonate, 0.1 mM non-essential amino acids, and 1.0 mM sodium pyruvate (95%) and (2) fetal bovine serum (5%). In certain cases, HEp-2 cells showed significantly better transfection rates than Vero cells.

Monoclonal antibodies (MAb) 6 and 19 were provided by Geraldine Taylor (Institute for Animal Health, Compton, United Kingdom), MAb L9 by Ed Walsh (University of Rochester School of Medicine, Rochester, N.Y.), and MAbs AcV1 and AcV5 by Gary Blissard (Boyce Thompson Institute at Cornell University, Ithaca, N.Y.). MAb 6 was against HRSV nucleocapsid (N) protein, MAb 19 was against HRSV F protein, MAb L9 was against HRSV G protein, and MAb AcV1 and AcV5 were against GP64. The anti-VSIV G antibody was a mouse ascitic fluid acquired from ATCC. The anti-vaccinia antibody was a polyclonal serum harvested from rabbits infected with vaccinia virus.

Example 2

Construction of a Chimeric GP64/HRSV F Protein

The AcMNPV GP64 gene sequence is obtainable from GenBank accession number NC_001623. See Ayres, et al., VIROLOGY, 202:586-605 (1994). A truncated GP64 ORF (anmino acids 1 to 505) flanked by a 3' XbaI restriction site was generated using PCR. Nucleotides encoding the C-terminal 12 amino acids (QLSGIN IAFSN, amino acid residues 3-15 of SEQ ID NO:2) of the HRSV F protein preceded by three nucleotides encoding an additional arginine residue to ensure proper membrane anchoring were amplified using PCR creating a 5' XbaI site. The introduced restriction site was utilized to ligate the two fragments resulting in chimeric ORF $GP^{64/F}$ (FIG. 3A).

The HRSV F protein is responsible for fusion and entry at the plasma membrane in a non-pH-dependent manner. By analogy to other negative strand viruses, the cytoplasmic tail domain of the HRSV F protein may play a role in the virus life cycle. The cytoplasmic tail domain of the F protein is approximately 22 amino acids, significantly longer than that of GP64 (RNRNRQY, SEQ ID NO:1). In this example, only the nucleotides encoding the C-terminal 12 amino acids of HRSV F were used to replace the nucleotides encoding the cytoplasmic tail domain of GP64. The resulting chimeric protein may have improved properties in glycoprotein incorporation, membrane fusion, budding, or morphology.

The present invention also contemplates the use of a chimeric GP64 protein comprising the full-length cytoplasmic tail domain of HRSV F. Preliminary evidence suggested that the resulting chimeric protein provided similar advantages as $GP^{64/F}$.

Example 3

Transient Expression and Membrane Fusion Analysis

To determine the ability of GP64 to function in mammalian cells, GP64 was independently expressed in HEp-2 cells and its membrane fusion capacity was assayed. For this purpose, the AcMNPV GP64 ORF was placed behind a CMV promoter in plasmid vector pRc-CMV (Invitrogen). In addition, the membrane fusion capacity of $GP^{64/F}$ was tested. GP64, when expressed alone in insect cells, can induce syncytium formation after brief exposure to low pH (such as at pH 4). This function is thought to mimic the events that occur after acidification of the endosome upon entry of baculovirus BV virions. Plasmids expressing GP64 or $GP^{64/F}$ were transfected into HEp-2 cells to examine simultaneously the relative surface expression levels of GP64 or $GP^{64}$/F and their ability to cause membrane fusion (FIGS. 3B and 3C). Transfected cells were incubated at both 37° C. and 33° C. because of the difference in temperatures typically used to grow these viruses: 37° C. for HRSV in mammalian cells and 28° C. for AcMNPV in insect cells. At 34 h posttransfection cells were incubated on ice with anti-GP64 MAb AcV1, which recognizes a conformation-dependent epitope, and relative GP64 and $GP^{64/F}$ surface levels were measured by cell ELISA (CELISA) (FIG. 3B). Similar levels of GP64 and $GP^{64/F}$ were detected, indicating that both proteins can be expressed and present at the cell surface in a native conformation. However, the amount of protein at the cell surface was significantly higher at 33° C. than at 37° C.

To assay membrane fusion capacity, duplicate wells incubated at 33° C. or 37° C. were exposed to PBS pH 5.0 for 3.5 min at 34 h posttransfection, and incubated for four hours in normal growth medium. Cells were then fixed in 4% paraformaldehyde, stained with Hoechst (Molecular Probes) to visualize nuclei, and examined for syncytium formation with a fluorescence microscope (FIG. 3C). At 33° C., cells transfected with either GP64 or $GP^{64/F}$ plasmids displayed extensive syncytium formation, showing that both proteins are fusion competent. Though present at the surface at similar levels (FIG. 3B), more syncytia per well were observed for authentic GP64 than for cells transfected with $GP^{64o}$ F. In contrast to 33° C., few syncytia formed in transfected cells incubated at 37° C., in agreement with the reduced levels of GP64 and $GP^{64/F}$ at the cell surface at that temperature.

In insect cells, the pH threshold of AcMNPV GP64 for membrane fusion was approximately 5.5. Because cytoplasmic tail domains have been implicated in the capacity of some viral membrane fusion proteins to cause syncytium formation, the pH threshold for GP64-induced membrane fusion in HEp-2 cells was examined. Both GP64 and $GP^{64/F}$ -transfected cells were incubated at 33° C. and exposed for 3.5 min to PBS with a pH ranging from 5.0 to 7.0 (FIG. 3D). Extensive syncytium formation was observed at pH 5.0. In contrast, at pH 5.4 syncytia were present but rare. At pH 5.6 or higher, syncytia were no longer observed, indicating that the pH threshold in HEp-2 cells was similar to that observed in insect cells, and that alteration of the cytoplasmic tail domain of GP64 did not necessarily affect this threshold (FIG. 3D).

Insect and mammalian cells differ in the capacity to glycosylate proteins, in particular in their ability to perform sialylation. Despite these and other differences such as pH and temperature, GP64 was expressed at the surface of mammalian cells and cable of inducing membrane fusion after exposure to low pH (FIGS. 3B and 3C). While for some viral envelope proteins, alterations in the cytoplasmic tail domain have been shown to affect the ability to induce membrane fusion, a chimeric GP64 containing the cytoplasmic tail domain of the HRSV F protein in place of its own efficiently induced membrane fusion. Moreover, the pH threshold of fusion for GP64 and GP$^{64/F}$ was unchanged from that of GP64 in insect cells (FIG. 3D). In contrast, lowering the temperature of incubation from 37° C. to 33° C. can optimize membrane fusion and surface expression. Although the underlying reasons for the temperature sensitivity have not been examined here, one possible explanation is misfolding and/or degradation of GP64 at 37° C.; GP64 is commonly expressed under insect physiological conditions (28° C.) and appears to have strong structure/function constraints. Thus, surface levels and membrane fusion capacity of GP64 may further increase at lower temperatures, such as below 33 ° C.

The detailed methods employed in the expression and membrane-fusion analyses are described below. HEp-2 cells were plated in 6 well dishes and transfected with plasmids encoding GP64 or GP$^{64/F}$ using Lipofectin (Invitrogen) for 8 h at 37° C., and then incubated at 33° C. or 37° C. At 34 h posttransfection, infected cultures were examined for glycoprotein surface expression or subjected to a syncytium formation assay. Relative surface levels of GP64 and GP$^{64/F}$ were measured with cell ELISA (CELISA). Briefly, plates were chilled and cells were incubated with MAb AcV1 for 1 h on ice. Cells were washed extensively with cold PBS to remove unbound antibody, and fixed with cold 4% paraformaldehyde for 10 min on ice and then shifted to room temperature and incubated for another 15 min. Next, cells were incubated with a horseradish peroxidase conjugated secondary antibody, washed, and incubated in 1 ml of 3,3', 5,5' tetramethylbenzidine substrate (Pierce). At various times after adding substrate, 100 µl aliquots were taken and added to 2M sulfuric acid in a 96 well plate to stop the reaction, and the optical density at 450 nm was determined in an ELISA plate reader. For membrane fusion analysis, duplicate wells of cells at 34 h posttransfection were incubated for 3.5 min in PBS pH 5.0. After 3.5 min, cells were incubated in normal growth medium at 33° C. for 4 h and fixed with 4% paraformaldehyde. Fixed cells were stained for 5 min with Hoechst reagent (Molecular Probes) and photographed on an Olympus IX70 inverted microscope. To determine the pH threshold for fusion, HEp-2 cells were transfected as above and exposed to PBS with a pH ranging from 5 to 7 for 3.5 min at room temperature. Cells were then incubated for 4 h in normal growth medium and fixed in 4% paraformaldehyde. Syncytia containing 5 or more nuclei were counted using phase contrast microscopy.

Example 4

Generation and Characterization of Engineered HRSVs Expressing GP64

Figure 4A:
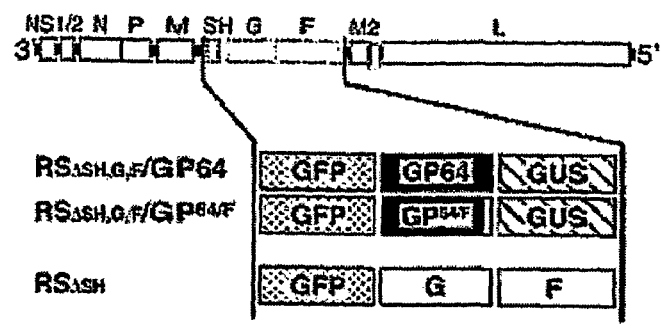
FIG. 4A shows the genome content of engineered viral cDNAs. In viruses $RS_{\Delta SH,G,F}/GP64$ and $RS_{\Delta SH,G,F}/GP^{64/F}$, the SH, G, and F open reading frames (ORFs) were deleted from the cDNA of the HRSV A2 strain and replaced with the ORF of GP64 or $GP^{64/F}$, respectively, along with ORFs encoding marker proteins GFP and GUS. Properties of these viruses were compared to virs $RS_{\Delta SH}$, a similarly engineered HRSV derived from the same A2 backbone, also containing GFP but having the homologous G and F ORFs in their native genome location.

To test whether GP64 can functionally complement an unrelated virus lacking all of its transmembrane glycoproteins, infectious HRSVs were generated in which all three HRSV glycoprotein ORFs were deleted and replaced with C)RFs encoding GP64 or GP$^{64/F}$ along with two placekeeper ORFs (GFP and GUS) (FIG. 4A). GFP encodes an enhanced green fluorescent protein (Clontech), and GUS encodes β-glucuronidase. In this manner, both the number and positions of genes were kept as in a wild-type HRSV, as the level of gene expression of nonsegmented negative-strand RNA viruses is controlled by the position of a gene relative to a single 3' promoter. Briefly, two shuttle vectors were constructed containing three ORFs (GFP-GP64-GUS or GFP-GP$^{64/F}$-GUS) separated by authentic HRSV intergenic junctions and flanked by unique restriction sites. These shuttle vectors were cloned into an SH/G/F-deleted cDNA containing matching restriction sites to yield cDNAs for the recovery of viruses that varied from wild-type HRSV only in the content of ORFs at gene positions six, seven and eight (pRS$_{\Delta SH,G,F}$/GP64 and pRS$_{\Delta SH,GF}$/GP$^{64/F}$, respectively) (FIG. 4A). As a comparison, an engineered virus was used in which the SH ORF was replaced with GFP but which contained wild-type HRSV G and F ORFs and replicated similarly to wild-type HRSV in cell culture (RS$_{\Delta SH}$ in FIG. 4A). The GP64- and GP$^{64/F}$-containing cDNAs were transfected into HEp-2 cells previously infected with MVA-T7, along with plasmids encoding the HRSV N, P, L, and M2-1 proteins, and infectious viruses were recovered from the supernatant and designated RS$_{\Delta SH,G,F}$/GP64 and RS$_{\Delta SH,G,F}$/GP$^{64/F}$, respectively. Virus stocks were generated in Vero cells at 33° C., yielding titers of approximately 10$^7$ PFU/ml. The genomes of virus stocks were verified by RT-PCR across the modified areas followed by sequence analysis at pass 3.

Figure 4B:
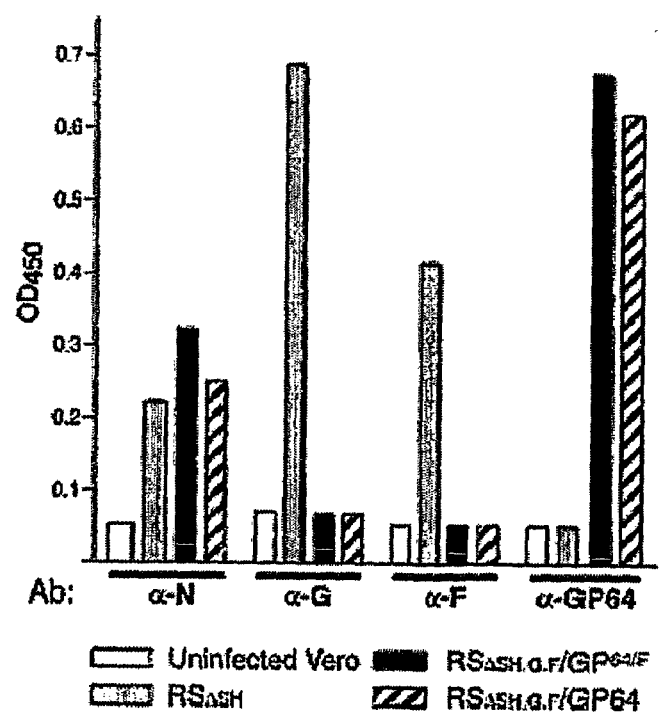
FIG. 4B illustrates the transmembrane glycoprotein expression of the engineered viruses detected using CELISA. Duplicate samples of cells infected with the indicated viruses were fixed and permeabilized at 28 h postinfection, and protein expression was measured by CELISA with antibodies against G (L9), F (MAb 19), GP64 (AcV5), or nucleocapsid protein (N) (MAb 6) as a control. OD450, optical density at 450 nm.

Expression of GP64 and/or HRSV G and F proteins in cells infected by each of the engineered viruses was examined. Infected Vero cells were fixed with paraformaldehyde at 28 h postinfection and permeabilized with 0.1% SDS. Cells were then incubated with antibodies against GP64 (AcV5), HRSV G (L9), HRSV F (MAb 19), or HRSV nucleocapsid (N) protein (MAb 6) as a control, and protein expression was measured by using CELISA (FIG. 4B). In cells infected with viruses RS$_{\Delta SH,G,F}$/GP64 and RS$_{\Delta SH,G,F}$/GP$^{64/F}$, the HRSV N protein, GP64, and GP$^{64/F}$ proteins were detected but not the HRSV G and F proteins, consistent with the gene content of these viruses. In contrast, virus RS$_{\Delta SH}$ infected cells demonstrated abundant expression of the HRSV N, G, and F proteins but not GP64 or GP$^{64/F}$. All viruses expressed GFP, as monitored by fluorescence microscopy, and GFP expression can provide an indicator of infectivity that correlate with PFU. These results confirmed that engineered viruses RS$_{\Delta SH,G,F}$/GP64 and RS$_{\Delta SH,G,F}$/GP$^{64/F}$ expressed GP64 and GP$^{64/F}$, respectively, as their transmembrane glycoprotein.

The methods for constructing viral cDNAs and recovering infectious engineered viruses are detailed below. A cDNA of the prototype A2 strain of HRSV was generated by RT-PCR of BRSV RNAs and cloned into plasmid pBluescript (Stratagene) using conventional cloning techniques. A T7 promoter followed by three guanosine residues to enhance transcription and a T7 terminator preceded by the hepatitis delta virus (HDV) ribozyme sequence were cloned on either side of the cDNA. Consequently, in the presence of the T7 polymerase, a plus-sense RNA is transcribed. From this transcript, viral genomic RNAs with precise 3' and 5' ends can be replicated by the viral polymerase, initiating an authentic viral infection.

Using conventional cloning techniques, the above-described cDNA-containing plasmid was modified by deleting the area from the translation initiation codon of SH to the translation termination codon of F, and inserting unique restriction sites (FseI and AscI) in its place (plasmid vector pRS$_{66 SH,G,F}$). A second plasmid vector named pSH/G/F was constructed, containing the exact HRSV genomic region deleted in pRS$_{\Delta SH,G,F}$, and also flanked by FseI and AscI restriction sites. The three open reading frames (i.e., SH, G, and F) contained within pSH/G/F were removed and each replaced with a linker containing unique restriction sites, creating construct pBLS-6,7,8. pBLS-6,7,8 thus contained intergenic regions, transcription signals, and 3' and 5' untranslated regions that were unaltered from those of virus A2. Specified glycoprotein and/or marker open reading frames were cloned into pBLS-6, 7, or 8 to generate shuttle vectors.

One shuttle vector contained three open reading frames GFP-GP64-GUS. Another shuttle vector contained open reading frames GFP-GP$^{64/F}$-GUS. These ORFs were separated by authentic HRSV intergenic junctions and flanked by unique restriction sites FseI and AscI. The resulting shuttle vectors were cloned into the pRS$_{\Delta SH,G,F}$ backbone via the FseI and AscI sites to generate the final cDNA-containing plasmids pRS$_{\Delta SH,G,F}$/GP64 and pRS$_{\Delta SH,G,F}$/GP$^{64/F}$ (FIG. 4B). The cDNA insert in each plasmid varied from wild-type HRSV only in the content of ORFs at gene positions six, seven and eight (i.e., SH, G, and F genes, respectively). Modified areas of the engineered cDNAs were verified by nucleotide sequencing. Likewise, plasmid PRS$_{\Delta SH}$ was prepared using standard cloning techniques. pRS$_{\Delta SH}$ contained the homologous human respiratory syncytial virus G and F open reading frames preceded by that of GFP.

Viruses were recovered from the cDNA as follows: HEp-2 cells (0.5×10$^6$ cells per well), infected with modified vaccinia Ankara-T7 virus (MVA-T7) at a multiplicity of infection of 5 for 1.5 h, were transfected with plasmids containing a modified HRSV cDNA and plasmids encoding each of the proteins required for transcription and replication of viral RNA (nucleocapsid protein [N], phosphoprotein [P], polymerase [L], and transcription factor M2-1), using Lipofectin (Invitrogen). For each transfection, 0.1 μg of cDNA plasmid was used, along with approximately 0.35, 0.2, 0.25, and 0.05 μg, respectively, of plasmids encoding the N, P, M2-1, and L proteins. Cells were incubated at 37° C. for 70 h, at which time supernatants were collected and added to fresh Vero cells. After 24 h at 33° C., the supernatant was replaced with fresh medium, and cells were incubated for another 7 days at 33° C. Virus was collected from the supernatants and amplified on Vero cells, and stocks were generated and stored at −80° C. Viral RNAs were harvested from cells infected with the engineered virus stocks at pass 3, amplified by RT-PCR and verified by nucleotide sequence analysis across cloning junctions and in modified areas. Pass 3 stocks can be used for further experiments. In certain cases, pass 5 stocks were used for RS$_{\Delta SH}$.

Example 5

Titration of Virus Stocks

Virus was adsorbed to cells for 1.5 hours at 37° C., then overlaid with 0.5% agar. At 5 days postinfection, 4% formaldehyde in PBS was added to the overlay, and incubated for 30 min at room temperature. Agar was removed and cells fixed for an additional 5 min in methanol. The protocol for visualization of antigens was a β-galactosidase detection assay. Fixed cells were incubated with either anti-GP64 antibodies (for viruses RS$_{\Delta SH,G,F}$/GP64 and RS$_{\Delta SH,G,F}$/GP$^{64/F}$) or anti-F antibodies (for viruses RS$_{\Delta SH}$ and virus A2), followed by incubation with a β-galactosidase conjugated goat-anti-mouse antibody (Southern Biotechnology Associates, Inc). After washing with PBS, cells were incubated overnight at 20° C. in a solution of 0.5 mM potassium ferricyanide/0.5 mM potassium ferrocyanide/0.1 mM MgSO4/0.15 mg/ml X-gal in PBS. Samples were washed twice with H$_2$O, dried, and plaques counted.

Example 6

Figure 5A:
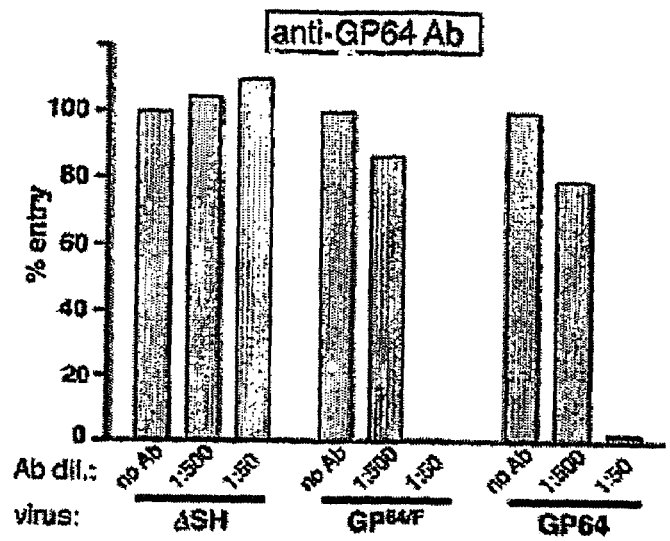
FIG. 5A indicates neutralization of infectivity by anti-GP64 antibody (Ab) AcV1. Viruses $RS_{\Delta SH}$, $RS_{\Delta SH,G,F}/GP^{64/F}$, and $RS_{\Delta SH,G,F}/GP64$ were preincubated with Ab AcV1, and used to infect Vero cells. After 22 h of incubation at 33° C., cells were trypsinized and examined for viral infectivity by quantitating GFP expression from the viral genome by flow cytometry. Bars represent relative entry, i.e., the number of GFP positive cells relative to the number of GFP expressing cells in the absence of antibody ×100, of duplicate samples. Antibody dilutions used are indicated.
Figure 5B:
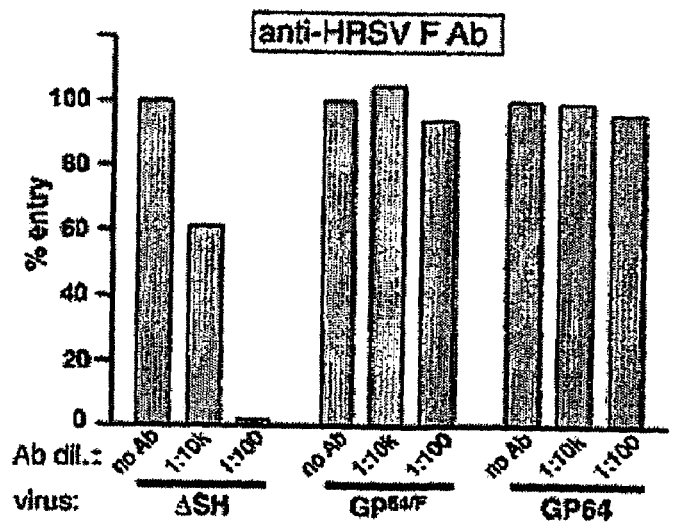
FIG. 5B indicates neutralization of infectivity by anti-HRSV F antibody (Ab) MAb 19. The neutralization effect was evaluated by using the same method as described in FIG. 5A.

Infectivity of Viruses RS$_{\Delta SH,G,F}$/GP64 and RS$_{\Delta SH,G,F}$/GP$^{64/F}$ To determine whether infectivity of viruses RS$_{\Delta SH,G,F}$/GP64 and RS$_{\Delta SH,G,F}$/GP$^{64/F}$ was mediated by GP64 and GP$^{64/F}$, respectively, the effect on virus entry of a characterized neutralizing anti-GP64 MAb (AcV1) was examined. Given quantities (1.5×10$^5$ PFU) of each of the engineered viruses were pre-incubated with MAb AcV1 at various concentrations for 70 min at room temperature and then used to infect 5×10$^5$ Vero cells. After infection cells were washed, incubated for 22 h at 33° C., trypsinized, and fixed, and the percentage of infected cells was determined by assaying for cells in which GFP was expressed from the engineered HRSV genomes by flow cytometry (FIG. 5A). MAb AcV1 inhibited entry of the GP64-containing viruses in a concentration-dependent manner, while virus RS$_{\Delta SH}$, which contains the HRSV G and F proteins and no GP64, was unaffected. In contrast, in the same assay MAb 19, an antibody specific for the HRSV F protein, inhibited infectivity of virus RS$_{\Delta SH}$ but not of viruses RS$_{\Delta SH,G,F}$/GP64 and RS$_{\Delta SH,G,F}$/GP$^{64/F}$ (FIG. 5B).

Figure 6A:
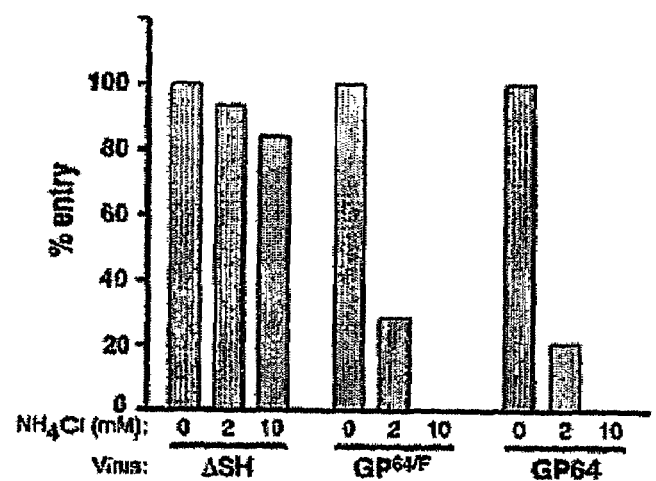
FIG. 6A shows the effect of ammonium chloride ($NH_4Cl$) on virus entry. Vero cells were infected for 1.5 h with viruses $RS_{\Delta SH}$, $RS_{\Delta SH,G,F}/GP^{64/F}$, or $RS_{\Delta SH,G,F}/GP64$ in the presence or absence of $NH_4Cl$, and further incubated at 33° C. maintaining the $NH_4Cl$ concentrations used during virus adsorption. At 22 h postinfection, cells were trypsinized, fixed, and examined for infectivity by measuring GFP expression by flow cytometry in duplicate. Bars represent the number of GFP expressing cells relative to the number of GFP expressing cells in the absence of $NH_4Cl$. $NH_4Cl$ concentrations used are indicated in millimnolars (mM).

The HRSV G and F proteins mediate pH-independent entry at the plasma membrane while entry mediated by the GP64 protein may require a low pH step. To determine whether replacement of the HRSV G and F proteins with GP64 or GP$^{64/F}$ rendered virus entry sensitive to compounds that buffer the endosomal pH, Vero cells were infected with the engineered viruses in the presence or absence of ammonium chloride (FIG. 6A). In many occasions, ammonium chloride can buffer the endosomal pH within one minute after addition to the cell medium, and does not affect binding, endocytosis, or membrane fusion. The presence of ammonium chloride blocked entry of viruses RS$_{\Delta SH,G,F}$/GP64 and RS$_{\Delta SH,G,F}$/GP$^{64/F}$ but not of virus RS$_{\Delta SH}$. This indicated that in contrast to virus RS$_{\Delta SH}$, the entry pathway of the GP64- and GP$^{64/F}$-containing viruses preferred low pH. The data of FIGS. 5A, 5B, and 6A indicate that infectivity of viruses RS$_{\Delta SH,G,F}$/GP64 and RS$_{\Delta SH,G,F}$/GP$^{64/F}$ can be mediated by GP64 in a low pH-dependent fashion.

As shown in Example 4, when the homologous HRSV glycoprotein ORFs were replaced with those of GP64 or GP$^{64/F}$, infectious viruses were recovered that expressed GP64 or GP$^{64/F}$ as their viral transmembrane glycoprotein. These viruses were effectively neutralized with GP64-specific antibodies. Thus in cell culture, the assembly-related functions provided by the HRSV transmembrane glycoproteins appear to be replaceable by heterologous viral glycoproteins. Consistent with the above mentioned low pH-mediated membrane fusion capacity in transfected cells, a low pH step facilitated GP64-mediated HRSV entry (FIG. 6A). This is in contrast to wild-type HRSV, which is thought to enter at the plasma membrane and not sensitive to compounds that buffer the endosomal pH. Thus, GP64 and GP$^{64/F}$ are able to convert the entry pathway of HRSV from a pH independent to a pH dependent one.

The detailed methods used for neutralizing infectivity or inhibiting virus entry are described below. For antibody-neutralization analysis, 1.5×10$^5$ plaque forming units (PFUT) of each of the engineered viruses were pre-incubated with MAb AcV1 or MAb 19 at a range of concentrations for 70 min at room temperature and then used to infect 5×10$^5$ Vero cells for 1.5 h at 37°C. Cells were washed, incubated for 22 h at 33°C., and examined for infectious virus by measuring GFP expression from the viral genome in duplicate with flow cytometry (FACSCalibur, Becton Dickinson), using 100,000 events per sample. To calculate relative entry, the number of cells expressing GFP in the presence of antibody was divided by the number of GFP-expressing cells in the absence of antibody and multiplied by 100.

For inhibition of entry analysis, Vero cells were infected with each of the engineered viruses at a multiplicity of infection of approximately 0.3 for 1.5 h in the presence of 0, 2, or 10 mM ammonium chloride. Ammonium chloride concentrations were maintained during postinfection incubation. At 22 h postinfection, cells were processed for flow cytometry. Relative entry was calculated by dividing the number of cells expressing GFP in the presence of ammonium chloride by the number of GFP-expressing cells in the absence of ammonium chloride and multiplying by 100.

For flow cytometry analysis, cells can be first trypsinized, resuspended in PBS, and pelleted in a microcentrifuge. Cells can then be resuspended in 4% paraformaldehyde and incubated for 20 min. Cells are pelleted, resuspended in PBS, and analyzed in a FACSCalibur flow cytometer.

Example 7

Kinetics of Virion Release From Endosomes

Figure 6B:
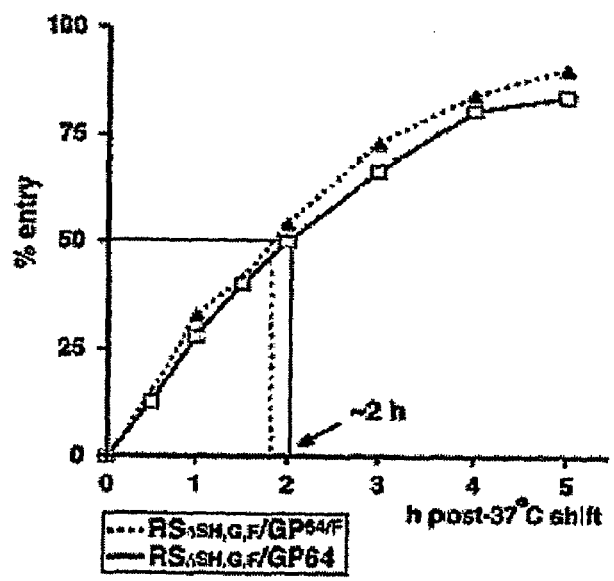
FIG. 6B depicts the timing of virion release from endosomes. Viruses $RS_{\Delta SH,G,F}/GP^{64/F}$ and $RS_{\Delta SH,G,F}/GP64$ were bound to Vero cells at 4° C. for 90 min, then replaced with medium pre-warmed to 37° C. (time 0). At time 0 or at 30-60 min intervals thereafter, ammonium chloride was added to the infected cells. At 20 h post 37° C.-shift, cells were harvested and the percentage of GFP-expressing cells was determined by flow cytometry. To calculate relative entry, the percentage of GFP-expressing cells for each sample was compared to the percentage of GFP-expressing cells in the absence of ammonium chloride and multiplied by 100. The time at which 50% of the bound virus was released from endosomes is indicated with an arrow.

Because of the fast acting buffering capacity of ammonium chloride, kinetics of nucleocapsid release from the endosome after internalization of a virus can be accurately determined by addition of ammonium chloride to cells at time intervals after synchronous virus binding. The kinetics of endosomal release may depend upon the pH at which a membrane fusion protein is triggered to induce fusion between the viral and endosomal membrane. The half-time of AcMNPV nucleocapsid release from the endosome after internalization in insect cells was reported to be approximately 25 min. In a mammalian cell type, PK1-LLC (Pk1), half-time of release of AcMNPV was reported to be approximately 50 min. In this example, the timing of endosomal release for viruses $RS_{\Delta SH,G,F}/GP64$ and $RS_{\Delta SH,G,F}/GP^{64/F}$ in Vero cells was determined (FIG. 6B). Virus was bound to cells at 4° C. for 90 min, then replaced with medium pre-warmed to 37° C. (time 0). Ammonium chloride was added to the infected cells at time 0 or at 30-60 min intervals thereafter. At 20 h post 37° C-shift, cells were harvested and the percentage of cells expressing GFP from the viral genome was determined by flow cytometry. The percentage of GFP-expressing cells of each sample was compared to the percentage of GFP-expressing cells in the absence of ammonium chloride to calculate relative entry and the time at which 50% of virions were released from endosomes. For both GP64-containing viruses, the half-time of endosomal release was approximately 2 h (FIG. 6B). This was significantly slower than that reported for GP64-mediated endosomal release of AcMPV in insect and PK1 cells. The similar half-time of release between viruses $RS_{\Delta SH,G,F}/GP64$ and $RS_{\Delta SH,G,F}/GP^{64/F}$ appears to be in agreement with the identical pH threshold for membrane fusion induced by GP64 and $GP^{64/F}$, as determined in FIG. 3D.

Although GP64-mediated infectivity of HRSV was efficient, the rate of nucleocapsid release for viruses RSΔSH,G, F /GP64 and RSΔSH,G,F /$GP^{64/F}$ (half-time of approximately 2 h) was markedly slower than that reported for AcMNPV in insect and mammalian cells (half-times of approximately 25 min and 50 min, respectively).

Among the possible explanations for the observed difference are cell type-specific differences, or sub-optimal GP64 function at 37° C. Another possibility may relate to the morphology of the HRSV infectious unit. In certain instances, infectivity can be lost after filtration though 0.45 μm filters, suggesting that the long filaments observed may be a predominant infectious form of HRSV. If this is the case, the length of the filaments also may be a factor in limiting the rate of entry via the endocytic pathway.

The following provides more detailed procedures used for determination of the kinetics of virion release. Vero cells ($0.4 \times 10^6$/well) were chilled to 4° C., and pre-chilled virus suspensions containing approximately $5 \times 10^5$ PFU were added and incubated for 90 min at 4° C. Inoculum was then removed and replaced with normal growth medium warmed to 37° C. (time 0). 10 mM ammonium chloride was added at the time intervals indicated in FIG. 6B. For time 0 samples, ammonium chloride was added when the inoculum was replaced with medium. Cells were incubated for 20 h at 37° C., and the percentage of cells expressing GFP from the viral genome was determined with flow cytometry and relative entry was calculated as described above.

Example 8

Incorporation of GP64 and GP64/F into HRSV Induced Filaments at the Cell Surface The GP64 and $GP^{64/F}$ proteins efficiently mediated infectivity of their respective viruses (FIGS. 5A, 5B, 6A, and 6B), indicating that these proteins incorporated into HRSV virions. The morphology of the infectious HRSV unit is not well defined. Both filaments of 4-10 μm in length and 80-150 nm in diameter, and spherical structures of the same diameter, which may or may not represent filament cross-sections, are observed in great abundance at the surface of infected cells. Because HRSV infectivity was shown to be predominantly cell-associated, and because the G and F proteins concentrate in the observed cell surface structures, it is generally believed that these structures represent infectious virus particles. This example examined (i) whether virally induced filaments were formed in the absence of any HRSV-specific glycoprotein components and (ii) whether $GP^{64/F}$ and authentic GP64 targeted to HRSV-induced filaments by immunoelectron microscopy (IEM) (FIGS. 7A, 7B, and 7C).

Vero cells at 27 h postinfection were fixed and incubated with MAb AcV5, followed by a secondary antibody conjugated to 6 nm-gold. As a negative control, cells infected with virus $RS_{\Delta SH}$ were subjected to the same procedure. IEM analysis of $RS_{\Delta SH}$ infected cells displayed the typical long filamentous and spherical structures (FIG. 7C). On higher magnification, spikes extending from the membrane surrounding the structures were visible; other studies have shown that these spikes consist of the HRSV G and F surface glycoproteins. In cells infected with viruses $RS_{\Delta SH,G,F}/GP64$ and $RS_{\Delta SH,G,F}/GP^{64/F}$, abundant filamentous and spherical particles of similar dimensions to those of wild-type and $RS_{\Delta SH}$ virus were observed; these viral structures were labeled across the entire surface after incubation with anti-GP64 antibodies and a gold-conjugated secondary antibody whereas particles at the surface of virus $RS_{\Delta SH}$ infected cells were not (compare FIGS. 7A and 7B to FIG. 7C). Thus both GP64 and $GP^{64/F}$ incorporated into HRSV induced structures at the cell surface. GP64 gold labeling was slightly more intense for virus $RS_{\Delta SH,G,F}/GP^{64/F}$ suggesting that inclusion of the 12 C-terminal amino acids of HRSV may aid the incorporation process.

Following wild-type HRSV entry and replication, the G and F proteins can be seen by electron microscopy to concentrate in cell-associated, virus-induced filamentous structures at the cell surface that are believed to represent virus particles.

In this example, an ORF was inserted into an SH,G,F-depleted HRSV genome. The ORF encodes a heterologous viral transmembrane glycoprotein carrying only a partial version of the cytoplasmic tail domain of the HRSV F protein ($GP^{64/F}$) or no HRSV cytoplasmic tail domain at all (authentic GP64). Both resulting engineered viruses ($RS_{\Delta SH,G,F}/GP^{64/F}$ and $RS_{\Delta SH,G,F}/GP64$, respectively) induced abundant cell surface filaments that contained $GP^{64/F}$ or GP64, respectively (FIG. 5). It is likely that the observed GP64- or $GP^{64/F}$-containing structures represent infectious virions, as the majority of infectivity of viruses $RS_{\Delta SH,G,F}/GP^{64/F}$ and $RS_{\Delta SH,G,F}/GP64$ remained cell associated (see FIG. 8C, below) and anti-GP64 antibodies neutralized infectivity (FIG. 5A). Since both GP64 and $GP^{64/F}$ efficiently mediated HRSV infectivity, it can be concluded that replacement of the GP64 cytoplasmic tail domain with a heterologous cytoplasmic tail domain is not required for incorporation of GP64 into HRSV filaments or infectivity in cell culture. However, as observed by IEM, the levels of $GP^{64/F}$ incorporated in the viral filaments were slightly higher than those of GP64. In addition, in the growth analysis (see FIGS. 8A and 8B, below), amplification of virus $RS_{\Delta SH,G,F}/GP^{64/F}$ at 37° C. was modestly but consistently higher than that of virus $RS_{\Delta SH,G,F}/GP64$, in particular during the first 24 hours of incubation in Vero cells. Thus, although not required in this system, the presence of the 12 C-terminal amino acids of the HRSV F protein may confer an advantage. The absence of a significant advantage for the HRSV F cytoplasmic tail domain in cell culture does not exclude the possibility of a role for this domain in wild-type HRSV replication in vivo. The fact that infectivity of these viruses remains associated with the cells in the presence of GP64 and absence of SH, G, and F suggests that HRSV components other than its transmembrane glycoproteins may also be involved in the cell-associated nature.

Interestingly, in the baculovirus BV phenotype, it appears that GP64 is localized at the ends of the rod-shaped virion. If the distribution of GP64 in baculovirus virions is indeed polarized, the relatively even distribution of GP64 across the HRSV filaments might suggest that in the BV or insect cell membranes, viral or cellular factors are in place to concentrate GP64 at the ends of the rod-shaped BV particle and/or to exclude it elsewhere in the viral membrane.

The following description illustrates the detailed method for carrying out the IEM analysis of this example. Vero cells infected with each of the engineered viruses at a multiplicity of infection of approximately 3 were fixed for 30 min at room temperature with 3% paraformaldehyde, 0.5% glutaraldehyde, 2 mM calcium chloride in PBS at 27 h postinfection. Cells were then incubated in 0.1% SDS for 5 min at room temperature to enhance epitope recognition by MAb Acv5, blocked for 10 min in 50 mM glycine and subsequently 30 min in 2% BSA, 0.1% cold water fish skin gelatin, 1% normal goat serum (Aurion). Cells were then incubated with antibody AcV5 in PBS, 0.1% BSA, washed, and incubated with a secondary goat-anti-mouse antibody conjugated to 6 nm-gold (Aurion). Cells were washed 4× in PBS, then fixed for 30 min in 2% glutaraldehyde, and washed again in PBS. Next, cells were fixed in 1% osmium tetroxide for 60 min, washed, dehydrated in a series of ethanol baths, and infiltrated in Polybed 812. Cut sections were lightly stained with uranyl acetate before examination and acquisition of images using a Hitachi H-7000 transmission electron microscope.

Example 9

The Effect of Temperature on Replication of Viruses $RS_{\Delta SH,G,F}/GP64$ and $RS_{\Delta SH,G,F}/GP^{64/F}$ The ability of the engineered viruses to replicate in mammalian cell cultures was examined (FIGS. 8A and 8B). Vero and HEp-2 cells were infected at a multiplicity of 0.5 and the production of infectious progeny virus was measured at 1-day intervals. Because GP64 cell surface and membrane fusion levels were higher at reduced temperature (FIG. 3B), growth characteristics at 37 and 33° C. were compared. Wild-type HRSV is known to remain predominantly cell-associated; to maximize viral yields virus was harvested by scraping cells into the supernatant followed by gentle pipetting. Viral titers were determined by 50% tissue culture infective dose ($TCID_{50}$) based on the expression of GFP. Virus $RS_{\Delta SH}$ replicated in Vero and HEp-2 cells to levels similar to that of a wild-type HRSV. In Vero cells, virus $RS_{\Delta SH}$ replicated to similar levels at 33° and 37° C., albeit that peak levels were reached sooner at 37 C., presumably due to the more rapid metabolism of cells at that temperature (FIG. 8A). For viruses $RS_{\Delta SH,G,F}/GP64$ and $RS_{\Delta SH,G,F}/GP^{64/F}$, production of infectious virus was consistently higher at 33° C. than at 37° C., in particular at day 4-6 postinfection (FIGS. 8A and 8B). This difference was even more pronounced in HEp-2 cells, where the levels of infectious virus produced at 33° C. were 100 to 1000 fold higher than those at 37° C. (FIG. 8B). Viruses $RS_{\Delta SH,G,F}/GP64$ and $RS_{SH,G,F}/GP^{64/F}$ amplified poorly at 37° C. in HEp-2 cells, and onset of virus production at 33° C. appeared delayed compared to virus $RS_{\Delta SH}$. The observed temperature sensitivity correlated with the increased levels of GP64 at the cell surface at reduced temperature (see FIG. 3B). Minor differences in replication were observed between the viruses containing authentic GP64 or $GP^{64/F}$. However, at 37° C., virus $RS_{\Delta SH,G,F}/GP^{64/F}$ replicated to moderately higher levels than virus $RS_{\Delta SH,G,F}/GP64$, indicating that the presence of the cytoplasmic tail domain of the F protein may confer an advantage.

The effects of replacement of the HRSV G and F proteins with GP64 on the predominantly cell-associated nature of HRSV infectivity were also examined. The supernatants and cell fractions of infected Vero cells were collected separately at a time where virus production was ongoing but no significant cell lysis had yet occurred (24 and 48 h postinfection), and virus titers were compared (FIG. 8C). The majority of $RS_{\Delta SH}$ infectivity (approximately 98-99%) was associated with the cellular fraction. Infectivity of the GP64-containing engineered HRSVs was also predominantly cell-associated, even though the baculovirus BV phenotype, of which GP64 is the major envelope glycoprotein, is efficiently secreted into the supernatant and stable in solution. Thus, GP64 may efficiently mediate infection of HRSV in two different mammalian cell types but did not alter the cell-associated nature of HRSV infectivity.

The results of the growth curves in FIGS. 8A and 8B appear to correlate with the temperature sensitivity of GP64 surface expression and membrane fusion (FIGS. 3B and 3C). Amplification of viruses $RS_{\Delta SH,G,F}/GP64$ and $RS_{\Delta SH,G,F}/GP^{64/F}$ at 33° C. was substantially higher than at 37° C. for both cell types examined, while replication of virus $RS_{\Delta SH}$ was not. Although temperature seems to be an important factor for GP64-mediated infectivity, the difference in replication efficiency at 37° C. and 33° C. was much more pronounced in HEp-2 cells than in Vero cells, suggestive of cell type-specific effects. Whether the observed differences are related to the expression, maturation, or incorporation of GP64 or other aspects of HRSV replication remains to be determined.

The detailed methods for constructing the growth curves of FIGS. 8A and 8B are described below. Vero and HEp-2 cells in 6 well plates were infected at a multiplicity of 0.5 for 1.5 h at 37° C., washed two times then incubated in 2 ml normal growth medium at 37 or 33° C. At 0 h postinfection and at 24 h intervals thereafter, one well for each condition was harvested by scraping the cells into the supernatant, and viral titers were determined in duplicate, without freezing the samples, by $TCID_{50}$ based on GFP expression from the viral genome (using 96-well plates with 10-fold dilution series with 12 replicate wells for each dilution). $TCID_{50}$ refers to the dilution stage at which 50% of the cell cultures employed would be infected. To determine the percentage of infectivity associated with the cellular and supernatant fractions, the supernatant of infected cells at 24 and 48 h postinfection was drawn off; an equal volume of fresh growth medium was then added to the cells and cells were then scraped into the medium, followed by gentle pipetting. The titers of both the cellular and supernatant derived virus suspensions were determined by $TCID_{50}$. The percentage of infectivity associated with the supernatant and the cell fraction was determined by dividing the respective titers by the combined titer of supernatant and cell-derived virus ×100.

EXAMPLEC 10

Stability of Infectivity Analysis

GP64 is a major structural component of the relatively stable baculovirus BV phenotype. Stocks of baculovirus AcMNPV BV can be stored at 4° C. for more than a year with infectivity virtually unchanged. In contrast, wild-type HRSV infectivity is notoriously unstable. See Fernie, et al, VIROLOGY, 106:141-144 (1980); and Gupta, et al., VACCINE, 14:1417-1420 (1996). Infectivity declines even when stored frozen and this is a significant problem for HRSV research and storage of potential vaccines. The cause of this instability is not known. Chemicals such as magnesium chloride and HEPES are generally added to increase stability. See Fernie, et al., supra; and Gupta, et al., supra.

Stocks of viruses $RS_{\Delta SH}$, $RS_{\Delta SH,G,F}$/GP64 and $RS_{\Delta SH,G,F}$/$GP^{64/F}$ were prepared simultaneously and identically from Vero cells infected at low multiplicity. Although deletion of the SH gene has no impact on replication of HRSV in cell culture, its role in virion stability has never been examined. Therefore, the wild-type A2 strain of HRSV (from which the engineered viruses were derived) also was included in this experiment. Infected cells were scraped into the medium, and this was followed by gentle pipetting and removal of cell debris by low speed centrifugation. Harvested stocks were divided into 100 µl aliquots, transferred to 4° C. for storage, and virus titers at day 0 determined in triplicate. To avoid possible effects of concentration on virus stability, some stocks were diluted to reach similar starting concentrations (average in $TCID_{50}$/ml at time 0: $RS_{\Delta SH}$, 3.4×10$^7$; $RS_{\Delta SH,G,F}$/$GP^{64/F}$, 3.2×10$^7$; $RS_{\Delta SH,G,F}$/GP64, 3.2×10$^7$; A2, 2.1×10$^8$). For these stocks, remaining infectivity was determined in triplicate by $TCID_{50}$ at 1-week intervals after storage at 4° C., and compared to the infectivity measured at the day of harvest (FIG. 9A). The infectivities of viruses $RS_{\Delta SH}$ and A2 declined rapidly. In average, more than 50% of the infectivity measured at the time of harvest was lost within three and a half days at 4° C., and after eight weeks of storage less than 4% of infectivity remained. In contrast, titers of viruses $RS_{\Delta SH,G,F}$/GP64 and $RS_{\Delta SH,G,F}$/$GP^{64/F}$ remain almost unchanged under the same storage conditions. Even after eight weeks at 4° C., infectivity was near 100% of that measured at the time of harvest. These data show that incorporation of GP64 in place of the homologous glycoproteins improved the stability of HRSV, and suggest that the HRSV transmembrane glycoproteins may be a factor in the instability of HRSV infectivity.

The stability of $RS_{\Delta SH,G,F}$/$GP^{64/F}$ infectivity at room temperature (about 22° C.) was also investigated. As shown in FIG. 9B, $RS_{\Delta SH,G,F}$/$GP^{64/F}$ stock remained at near 100% of the input level after storage at room temperature for six weeks. This room temperature stability offers the potential of reducing the problems associated with the availability and cost of cold chain equipment, which are significant in particular in third world countries. The stability of viruses containing GP64 but provided from Vbac cells in trans rather than expressed from the genome has also been examined. Virus $RS_{\Delta SH,G,F}$ with GP64 in the envelope via growth in Vbac cells exhibited high stability at 22° C. whereas viruses without GP64 rapidly lost infectivity. These viruses were also examined for stability at 37° C. While virus $RS_{\Delta SH}$ lost more than 99% of its infectivity in one week at 37° C., virus $RS_{\Delta SH,G,F}$/$GP^{64/F}$ was significantly more stable under the same conditions, retaining at least 20% of its infectivity. Additionally, providing $GP^{64/F}$ in trans to virus $RS_{\Delta SH}$ also significantly improved the stability of the recombinant virus.

The procedures used in the stability analysis of this example are detailed below. Virus stocks for each of the engineered viruses and wild-type A2 virus were generated simultaneously by infecting Vero cells at a multiplicity of infection of <0.2. Stocks were harvested by scraping cells into the supernatant, followed by gentle but extensive pipetting and removal of cell debris by low speed centrifugation. Stocks were distributed in 100 µl aliquots and stored at 4° C. or room temperature. In addition to undiluted stocks, diluted stocks were prepared by mixing undiluted stocks 1:6 with the supernatant of uninfected Vero cells grown in parallel and harvested identically to the virus stocks. Titers of all prepared stocks were determined in triplicate immediately after harvest and also at 3.5 and 7 days post harvest by $TCID_{50}$. This was done based on GFP expression for the engineered viruses and by an immunoassay based on the F protein for virus A2. In the case of virus A2, cells were fixed with paraformaldehyde, incubated with a mixture of anti-G and anti-F antibodies followed by a secondary antibody with a fluorescent conjugate, and then scored with a fluorescence microscope. To test whether GFP expression correlated with replicating engineered virus, plaque assays can be first scored for GFP expression, and then the cells are fixed and scored for GP64 expression via antibodies using standard plaque assay techniques. Marked plaques expressing GFP preferably overlap precisely with plaques identified via GP64. As a control, at every time point, titers of virus $RS_{\Delta SH}$ were determined by both methods described above; the two methods yielded identical viral titers. Stocks with similar starting concentrations were selected for continuation of the stability experiment to minimize concentration effects. Viral titers of these stocks were subsequently determined at week 2, 3, 4, 6, and 8 after harvest as above. Relative titers were calculated by dividing the $TCID_{50}$ score at each time point by the titer determined at the time of harvest and multiplying by 100.

Example 11

Generation of a Stable Cell Line Expressing the Baculovirus GP64 protein.

In order to generate an HRSV lacking the SH, G, and F glycoprotein genes for the purpose of examining virus transmission in the absence of viral transmembrane glycoproteins, a stably transfected cell line was generated which can provide a heterologous replacement protein in trans. $GP^{64/F}$ was used as a replacement protein. As demonstrated above, $GP^{64/F}$ can be expressed efficiently from a nuclear promoter, and show no signs of cytotoxicity to cultured cells. Moreover, infectivity of an SH/G/F-depleted HRSV containing $GP^{64/F}$ was highly stable compared to a wild-type HRSV.

A plasmid, constructed to express both the $GP^{64/F}$ protein and a neomycin resistance gene, was used to transfect early passage Vero cells. After prolonged incubation at 33° C., G418-resistant colonies were selected, expanded, and tested for expression by immunofluorescence (IF) with anti-GP64 MAb AcV5. Cells from colonies expressing the highest level of $GP^{64/F}$ were then subjected to two rounds of subcloning via limiting dilution and screening by indirect IF. Finally, one cell line constitutively expressing $GP^{64/F}$ was selected and designated Vbac, pass 1. The Vbac cells appeared to be larger and have a lower cell division rate than the Vero cells from which they were derived. FIGS. 10A and 10B demonstrate the expression of $GP^{64/F}$ in Vbac cells at pass 8, compared to the parental Vero cell line. Cells on ice were incubated with anti-GP64 MAb AcV1, washed with cold medium, and fixed with 4% paraformaldehyde. After fixation, cells were incubated with an alexa594-conjugated secondary antibody, stained with Hoechst (to visualize nuclei), and photographed on a fluorescence microscope (FIG. 10A). Vbac cells were also detached from plates with 5 mM EDTA, fixed and labeled as above, and examined for $GP^{64/F}$ expression using flow cytometry (FIG. 10B). The data of FIG. 10A and 10B show that all cells within the Vbac population expressed the $GP^{64/F}$ protein, and that expression levels between cells varied. When Vbac cells were maintained in medium containing G418, the level and distribution of $GP^{64/F}$ expression remained relatively constant for at least 10 passages.

The detailed methods for producing stably transfected Vbac cells are provided below. An ORF expressing chimeric protein $GP^{64/F}$ was constructed using standard molecular biology techniques, and cloned into expression vector pRc/CMV (Invitrogen). The resulting plasmid (pRc-$GP^{64/F}$), expressing both the $GP^{64/F}$ and a neomycin resistance gene, was transfected into Vero cells at pass 5, using lipofectamine 2000 (Invitrogen). Cells were incubated at 33° C. The following day, transfected cells were detached and plated in 6 well plates at various densities. At 48 h posttransfection, 1 mg/ml of G418 sulfate (Geneticin, Invitrogen) was added to the medium, and cells were further incubated at 33° C. G418-resistant colonies were selected between 18 and 34 days later, expanded, and tested for $GP^{64/F}$ expression using anti-GP64 MAb AcV5 and indirect immunofluorescence. A number of $GP^{64/F}$-positive colonies were subject to two rounds of subcloning by plating detached cell suspensions at 1 cell/well in 96 well plates, and continued incubation at 33° C. in medium containing G418 sulfate. Following the two rounds of subcloning, a final $GP^{64/F}$-positive cell line was selected (#116-25-1) and designated Vbac, pass 1. Throughout this procedure, Vbac cells were maintained in standard growth medium containing 5% FBS, 1 mg/ml G418 sulfate, and 25 mM HEPES at 33° C. For characterization of the Vbac cell line, cells were attached to glass cover slips, chilled, and incubated with MAb AcV1 1:20 in PBS, 01% BSA, for 1 h on ice. Unbound antibody was removed by four wash steps with cold PBS, and cells were fixed with cold 4% paraformaldehyde for 10 min, then transferred to room temperature and incubated another 15 min in 4% paraformaldehyde. Cells were washed, blocked with PBS, 2% BSA, and 0.1 % cold water fish skin gelatin for 1 h at room temperature, and incubated with a goat-anti-mouse antibody carrying an alexa-594 fluorescent conjugate (Molecular Probes) for 50 min at room temperature. Cells were washed with PBS, stained for 10 min with Hoechst reagent (Molecular Probes) to visualize nuclei, mounted and photographed on an Olympus IX70 inverted microscope. For flow cytometry, Vbac cells were detached in 5 mM EDTA, chilled, and incubated with antibodies (without Hoechst treatment). After the last wash, cells were resuspended in 500 µl PBS, and analyzed in a FACSCalibur flow cytometer (Becton Dickinson), using 50,000 events per sample.

For flow cytometry analysis, cells were trypsinized, washed, fixed with 4% paraformaldehyde, and analyzed in an FACSCalibur flow cytometer (Becton Dickinson), using 50,000 events per sample.

Example 12

Generation and Characterization of Glycoprotein-Deleted HRSVs

To generate glycoprotein deleted HRSVs, two cDNAs were constructed from the A2 strain of HRSV. In one cDNA, the SH, G, and F ORFs were deleted and replaced with the ORFs of three marker proteins, GFP, CAT and GUS, respectively (pRS$_{\Delta SH,G,F}$) (FIG. 11A). CAT denotes chloramphenicol acetyltransferase. This HRSV cDNA encoded no viral envelope proteins. In the second cDNA, the SH and F ORFs were replaced with GFP and GUS, respectively, but the HRSV G protein ORF remained in its native position (pRS$_{\Delta SH,F}$) (FIG. 11A). Though altered in genome positions six, seven, and eight, both cDNAs retained fully wild-type intergenic junctions throughout. For recovery of infectious virus, the engineered cDNAs were transfected into HEp-2 cells previously infected with MVA-T7, along with plasmids encoding the N, P, L, and M2-1 proteins (FIG. 11B). To enable the virus to be passaged from the infected/transfected HEp-2 cells, an additional plasmid encoding $G^{VSV}$ was included. $G^{VSV}$ is a chimeric VSWV G protein from which the cytoplasmic tail domain was exchanged with that of the HRSV F protein. Supernatants from infected/transfected HEp-2 cells were transferred onto Vbac cells and GFP-expressing spreading foci were observed upon incubation at 33° C. The viruses harvested from the first round of Vbac cells, designated RS$_{\Delta SH,G,F}$ or RS$_{\Delta SH,F}$, were incubated with anti-vaccinia and anti-VSIV G antibodies to neutralize virus that may have carried over via the use of the VSIV G plasmid included in the transfection. Next, these antibody-treated stocks were further amplified by one additional round of growth in Vbac cells. Virus stocks were harvested and verified by RT-PCR across the modified areas followed by sequence analysis at pass 3. In Vbac cells, both viruses yielded stock titers of approximately 2×10$^6$ PFU/ml, approaching titers generally reported for wild-type HRSV stocks.

To examine the glycoprotein expression by each of the engineered viruses, infected Vero cells were incubated at 33° C., and fixed and permeabilized at 28 h postinfection. Cells were incubated with antibodies against GP64 (AcV5), HRSV G (L9), HRSV F (MAb19), or HRSV nucleocapsid (N) protein (MAb6) as a control, and protein expression was measured using CELISA as previously described (FIG. 12). As control viruses, $RS_{\Delta SH,G,F}/GP^{64/F}$ and $RS_{SH}$ were used. In addition to N protein, virus $RS_{\Delta SH,F}$ expressed the HRSV G protein but not F or GP64; virus $RS_{\Delta SH,G,F}$ did not express any transmembrane glycoprotein, as expected. In contrast to Vero cells, in Vbac cells infected with engineered viruses $RS_{\Delta SH,G,F}$ or $RS_{\Delta SH,F}$,$GP^{64/F}$ was detected as this protein is provided by the cell line (FIG. 12). These results showed that the glycoprotein expression was in agreement with the genome content shown in FIG. 11A, and that $GP^{64/F}$ production in the Vbac cell line continues after infection with the engineered HRSVs.

The methods used for cDNA construction, HRSV recovery and gene expression detection are further described below. Engineered cDNAs were generated based on a cDNA of the A2 strain of HRSV. Two shuttle vectors were first constructed containing three ORFs (GFP-CAT-GUS or GFP-G-GUS) separated by authentic HRSV intergenic junctions and flanked by unique restriction sites FseI and AscI. These shuttle vectors were cloned into an SH/G/F-deleted cDNA backbone also containing FseI and AscI restriction sites to yield cDNAs that varied from wild-type HRSV only in the content of ORFs at gene positions six, seven and eight ($pRS_{\Delta SH,G,F}$ and $pRS_{SH,F}$, respectively). Modified areas of the engineered cDNAs were verified by nucleotide sequencing. Infectious viruses were recovered from cDNA as described above with the following exceptions: (i) in the initial transfection, 0.1 µg of a plasmid was included encoding $G^{VSV}$; and (ii) instead of Vero cells, generated viruses were amplified in Vbac cells. At pass 2, recovered viruses were incubated with anti-VSIV G ascitic fluid (1:100 dilution) and anti-Vaccinia serum (1:50) for 1 h at room temperature, then used for the production of pass 3 stocks. Viral RNAs were harvested from cells infected with the engineered virus stocks at pass 3, amplified by RT-PCR and verified by nucleotide sequence analysis across cloning junctions and in modified areas. Pass 3 stocks were used for other studies.

Protein expression by the engineered viruses was examined by CELISA. Vero or Vbac cells infected with the engineered viruses at a multiplicity of 2 were fixed with 4% paraformaldehyde for 15 min at 28 h postinfection and permeabilized by incubation with 0.1% SDS for 5 min at room temperature. Cells were then incubated with antibodies against GP64 (AcV5), HRSV G (L9), HRSV F (MAb19), or HRSV nucleocapsid (N) protein (MAb6) as a control, washed, and incubated with a horseradish peroxidase conjugated secondary goat-anti-mouse antibody (Pierce). Next, cells were washed and incubated in 1 ml 3,3', 5,5' tetramethylbenzidine substrate (Pierce). At various times after adding substrate, 100 µl aliquots were collected and added to 2M sulfuric acid in a 96 well plate to stop the reaction, and the optical density at 450 nm was determined in an ELISA plate reader. As a positive control for the HRSV F protein, $RS_{\Delta SH}$ virus which expresses the wild-type HRSV G and F proteins was included.

Example 13

Virus Transmission in Cell Culture

HRSV viruses from which the SH, G, or both genes were deleted and not replaced can propagate efficiently in Vero cells. Circumstantial evidence points to a potentially critical role for the F protein in virus infectivity. By providing heterologous protein $GP^{64/F}$ protein from a cell line to glycoprotein-depleted engineered viruses, HRSV transmission in cell culture in the absence of the F protein (or another functional entry/exit protein) can be monitored. Vero or Vbac cells, plated at about 60% confluency, were infected with viruses $RS_{\Delta SH,G,F}$ and $RS_{\Delta SH,F}$ at a multiplicity of 0.05, incubated at 33° C., and examined for GFP expression at daily intervals (FIG. 13). GFP expression from the same position within the genome of an infectious engineered HRSV can be an accurate indicator of infectivity that correlate with plaque forming units. To document spread to neighboring cells, the infected cultures were photographed on a fluorescence microscope on day 1, 2, 4, and 6 postinfection (FIG. 13). Vero cells infected with a virus containing the $GP^{64/F}$ ORF within its genome ($RS_{\Delta SH,G,F}/GP^{64/F}$) were included. Viruses $RS_{\Delta SH,G,F}$ and $RS_{\Delta SH,F}$ spread rapidly in Vbac cells; by day 6, all cells in the cultures displayed green fluorescence. The rate of spread appeared similar to that of control virus $RS_{\Delta SH,G,F}/GP^{64/F}$ in Vero cells (bottom panels of FIG. 13). In contrast, minimal spread to neighboring cells was observed in Vero cell cultures infected with viruses $RS_{\Delta SH,G,F}$ and $RS_{SH,F}$. Although the viruses appeared to spread between day 1 and 2, no increase in the number of cells displaying green fluorescence was observed after day 2. The intensity of fluorescence in infected cells increased over time, resulting in very brightly fluorescing single cells by day 4. This appears to be in agreement with the fact that these viruses are fully competent for RNA transcription and replication but are unable to spread to neighboring cells. These results indicate that, in contrast to the SH and G proteins, the F protein might be critical for HRSV transmission in cell culture, and that expression of the G protein alone does not rescue the transmission deficiency. The small increase in the number of fluorescing cells between day 1 and 2 might be the result of cell division, as cells continued to divide rapidly until reaching confluency.

The detailed protocols for evaluating virus transmission in cell culture are described below. Vero or Vbac cells were plated in 6 well plates at approximately 60% confluency, infected at a multiplicity of 0.05 for 1.5 h, and incubated at 33° C. On day 1, 2, 4, 6, and 8 postinfection, one well for each condition was fixed in 4% paraformaldehyde for 15 min, and examined for GFP expression on an Olympus IX70 inverted microscope. GFP expression provides an accurate indicator of virus infectivity that correlates with PFU. Fixed cell cultures were photographed at 200x magnification.

Example 14

Production of Infectious Progeny Virus

Example 13, which shows both expression of GFP and an inability to spread in Vero cells, indicates that viruses $RS_{\Delta SH,G,F}$ and $RS_{\Delta SH,F}$ can enter and replicate their genomes, but are incapable of producing infectious virions. To verify the latter, the yield of infectious virus produced in Vbac cells, Vero cells, and HEp-2 cells were compared (FIGS. 14A-14C). Cells were infected with each of the viruses used in FIG. 13 at a multiplicity of 0.25, washed two times, and then incubated at 33° C. Immediately after infection (day 0), or at 2 and 4 days postinfection, cells were scraped into the supernatant, mixed by pipetting, and titrated on Vbac cells by $TCID_{50}$ based on the expression of GFP. In Vbac cells, viruses $RS_{\Delta SH,G,F}$ and $RS_{\Delta SH,F}$ replicated to similar titers to that of control virus $RS_{\Delta SH,G,F}/GP^{64/F}$, which contains the $GP^{64/F}$ gene within its genome and is capable of yielding higher titers than a virus containing the wild-type G and F proteins in Vero cell cultures (FIG. 14A). For each virus, the majority of infectivity was associated with the cell fraction similar to a wild-type HRSV. In contrast to Vbac cells, when viruses $RS_{\Delta SH,F}$ and $RS_{SH,G,F}$ were used to infect Vero and HEp-2 cells, the yield of infectious virus increased by approximately 2 orders of magnitude less than in the Vbac cells (FIG. 14A). This reduction in infectious virus yield was consistent with the results of FIG. 13, confirming the potentially critical nature of the F protein for virus infectivity. Nevertheless, an approximately 10-fold increase in titers of viruses $RS_{\Delta SH,G,F}$ and $RS_{\Delta SH,F}$ was measured in Vero and HEp-2 cells even in the absence of viral transmembrane glycoproteins, when titrated in Vbac cells. To examine whether the observed increase in infectivity represented specific virus entry or non-specific uptake by the Vbac cells, stored samples of from the growth curves of viruses $RS_{\Delta SH,G,F}$ and $RS_{\Delta SH,G,F}/GP^{64/F}$ grown in HEp-2 or Vero cells (FIG. 14A) were used to infect Vbac cells and Vero cells simultaneously, and then titrated using $TCID_{50}$ (FIG. 14B). In addition to $TCID_{50}$, parallel samples were examined with flow cytometry for expression of GFP as a measure of viral entry (FIG. 14C). The results of FIG. 14B confirmed that, when titrated on Vbac cells, a modest increase in infectivity is observed for virus $RS_{\Delta SH,G,F}$ grown in Vero or HEp-2 cells. In contrast, when titrated on Vero cells, $RS_{\Delta SH,G,F}$ titers declined immediately after infection, while those of virus $RS_{\Delta SH,G,F}/GP^{64/F}$ did not. Similarly, the percentage of entry of virus $RS_{\Delta SH,G,F}$ into Vbac cells increased to 1.54% from day 2 to 4 postinfection, while no entry was observed in Vero cells (FIG. 14C). Combined, these data show that virus $RS_{\Delta SH,G,F}$ does not produce infectious virions when grown in Vero or HEp-2 cells, in agreement with the block in cell to cell transmission documented in FIG. 13. The low level infectivity observed in FIG. 14A might be due to uptake of virions lacking any transmembrane glycoproteins via the $GP^{64/F}$ protein expressed at the Vbac cell surface. Interestingly, the percentage of $RS_{\Delta SH,G,F}/GP^{64/F}$ entry into Vbac cells was lower than into Vero cells, indicating that the $GP^{64/F}$ protein at the Vbac cell surface might also interfere with the ability of a GP64-containing virus to enter.

The following protocol details the construction of the above-described growth curves. Vero, Vbac, and HEp-2 cells were infected in 6 well plates at a multiplicity of 0.25 for 1.5 h at 33° C., washed twice, and then incubated in 1.5 ml normal growth medium at 33° C. At day 0, 2, and 4 postinfection, the supernatant of infected cells was drawn off, and an equal volume of fresh growth medium was added to the cells. Cells were then scraped into the medium, followed by gentle pipetting. The titers of both the supernatant and cell derived virus suspensions were determined in Vbac or Vero cells by $TCID_{50}$ based on GFP expression.

The above examples demonstrate the effectiveness of the $GP^{64/F}$ complementation system to support in trans the transmission of HRSV from cell to cell in the absence of the SH, G, F, or other heterologous viral envelope proteins. The results provide direct evidence and confrm the general assumption that F may be critical for the transmission of HRSV in cell culture. $GP^{64/F}$, provided in trans to HRSVs lacking the F protein gene, allowed entry and viral replication into Vero cells, but these viruses subsequently failed to spread to neighboring cells (FIG. 13). As a result, the majority of cells within the infected cultures remained healthy and dividing. A virus containing HRSV G gene behaved similarly to one lacking all three transmembrane glycoproteins, indicating that the G protein alone might not be sufficient to allow virus transmission. In contrast to certain other cultured cell lines, Vero cells allowed relatively efficient amplification of an HRSV lacking the G gene. However, HRSV spread in Vero cells as well as in HEp-2 cells was impaired in the absence of the F protein (FIGS. 13 and 14A). These results suggest that for virus transmission in cell culture, the F protein may have an important role. This appears to be in agreement with earlier work involving a helper-dependent mini-replicon system, in which the viral nucleocapsid, the matrix protein, and the F protein were found to be the minimal components for the production of infectious virus. See Teng and Collins, JOURNAL OF VIROLOGY, 72:5707-5716 (1998).

It is not known whether the absence of the three transmembrane glycoproteins results in a block in virus budding or whether budding continues resulting in naked, non-infectious virus particles. The low level infectivity in Vbac cells of viruses $RS_{\Delta SH,G,F}$ and $RS_{\Delta SH,F}$ grown in Vero or HEp-2 cells suggest that virus particles may continue to form even in the absence of the SH, G, and F proteins. Preliminary evidence using IF microscopy supports this suggestion.

The GP64-based trans-complementation system provides a preferred approach for the development of safe HRSV vaccines. Current HRSV vaccine approaches are mostly based on live-attenuated viruses. These live candidates contain a series of debilitating point mutations to reduce disease while still eliciting an immune response. However, it has proven challenging to find an acceptable balance between immunogenicity and safety, and some of the point mutations have been shown to revert to wild-type. The ability to generate infectious virus by complementation with a heterologous viral protein from a cell line constitutes an alternative approach towards improving vaccine safety. This because (i) HRSVs lacking a functional F protein gene are impaired in their ability to spread to neighboring cells (but are not attenuated for replication and transcription and thus will express viral antigens after initial entry via the GP64 or $GP^{64/F}$ protein provided by the complementary cell line, and (ii) trans complementation removes finctional constraints on the G and F protein, allowing one to selectively include G and F protein domains or epitopes into an engineered genome. Moreover, HRSV infectivity mediated by the GP64 or $GP^{64/F}$ protein is significantly more stable than that of a wild-type HRSV. Thus the approach of mediating HRSV infectivity via heterologous viral proteins in trans provides the needed balance between safety and efficacy, and improves the stability of HRSV, two key problematic areas in the design of live-attenuated vaccines.

Example 15

Development of Recombinant or Multipurpose Vaccines

To date, it has been proven challenging to find an acceptable balance between immunogenicity and the safety of live HRSV vaccine candidates. Many tested vaccine candidates that were sufficiently immunogenic were either over- or under-attenuated, and showed adverse effects not acceptable within the context of a vaccine. The ability to generate infectious virus by complementation with a heterologous viral protein from a cell line provides new opportunities to address vaccine safety without comprising antigenicity. With the Vbac cell system, viruses can be generated which are impaired in cell-to-cell transmission yet not attenuated for replication and expression of viral antigens. Trans-complementation also removes the dependence on functional G and F proteins for virus propagation and stock production, allowing one to include selected G and F protein domains or epitopes (or nonfunctional versions of these proteins) into an engineered viral genome. When included in the engineered HRSV genome, the $GP^{64/F}$ protein conferred onto the virus a temperature-sensitive phenotype, with reduced propagation at 37° C. These features, together with enhanced HRSV stability via the use of the $GP^{64/F}$ protein, provide new strategies to establish a balance between safety and efficacy and to improve the stability of HRSV, two problematic areas in the design of live attenuated vaccines.

Furthermore, the strategy of providing GP64 protein in trans to generate replication-competent but transmission-deficient HRSVs can be employed to generate multipurpose vaccines. Immunoprotective epitopes from any disease-causing virus or microbe can be included in the genome of a transmission-deficient HRSV. The resulting HRSV is infectious, replicable, and capable of abundantly expressing the selected epitopes within infected cells. However, the engineered HRSV is incapable of spreading to other cells, thereby reducing the risk of causing adverse disease symptoms.

An engineered virus of the invention can be administered to human subjects according to well established protocols. See, for example, Wright, et al, INFECT. IMMUN., 37:397-400 (1982). In one instance, adults or children are inoculated intranasally via droplet with $10^2$ to $10^9$ PFU, preferably $10^4$ to $10^5$ PFU, of the engineered virus. Antibody response is evaluated by complement fixation, plaque neutralization, ELISA, or any other suitable technique. Individuals are monitored for signs and symptoms of upper respiratory illness. Subsequent immunizations can be administered periodically to the individuals as necessary to maintain sufficient levels of protective immunity.

Example 16

Modifications in the HRSV F Protein Cytoplasmic Tail and Transmembrane Domains for the Production of Live-Attenuated HRSV Vaccines Using the Vbac Cell Line The above examples demonstrate that the Vbac cell line allows for the production of infectious HRSVs that carry F genes that are either non-functional or poorly functional. In this example, Vbac cells were used to generate HRSVs in which the level of cell-to-cell transmission was fine-tuned through modification of the F protein. These F protein modifications resulted in significantly attenuated HRSVs that have potential as vaccine candidates.

HRSVs were constructed in which the F gene was modified and the SH gene was replaced with GFP gene. These modified-F expressing viruses fell into two categories (FIG. 15). The first category (Group A in FIG. 15) included viruses with a fusion-competent F protein and limited cell-to-cell transmission. The viruses in Group A category lack the homologous F protein cytoplasmic tail domain (e.g., $F_{\Delta CTD}$), have the homologous F protein cytoplasmic tail domain replaced with that of the VSV G protein (F/vG-CTD), or lack both the transmembrane and cytoplasmic domains of F and carry those of the VSV G protein instead (e.g., F/vG-TM+CTD). The viruses in Group A can replicate their RNA, which is necessary for production of sufficient antigen, but generate only very low levels of progeny virions in cell cultures (FIG. 16, where RSΔCTD and RS/vG-CTD express $F_{\Delta CTD}$ and F/vG-CTD, respectively). This provides a safety factor compared to viruses replicating at wild-type levels (RS-wt F in FIG. 16, which expresses $F_{WT}$, the wild-type F protein). Despite their low levels of cell-to-cell transmission in cell culture, the viruses in Group A have fusion-competent F proteins, indicating that the F proteins are in a mature state of oligomerization and processing and thus are likely to comprise good antigens for vaccination and immune protection. Moreover, the F proteins that lack their homologous cytoplasmic tail domains are displayed at the cell surface in a much higher proportion than the wild type F protein, therefore providing enhanced immune presentation. The recombinant viruses in Group A can be produced in Vero or other cultured cell lines, in addition to Vbac cells.

The viruses in Group B have fusion-incompetent F proteins and therefore are incapable of cell-to-cell transmission (FIG. 15). These viruses lack the homologous F protein cytoplasmic tail domain, transmembrane domain, and a small portion of the F ectodomain. For instance, F/vG447-511 lacks the endogenous F protein amino acids 505-574 (encoding the cytoplasmic tail domain, transmembrane domains, and the C-terminal portion of the ectodomain) and have these sequences replaced with the corresponding region of the VSIV G protein, either with or without the cytoplasmic tail domain (amino acids 447-511 and 447-491, respectively). Viruses expressing the modified F proteins of Group B were not fusion competent, but importantly, still expressed the F proteins at the cell surface. These viruses did replicate their RNA once entered the cells, but did not spread from cell-to-cell in cell cultures. As a consequence, these viruses offer the advantage of being severely restricted in cell-to-cell transmission, and provide opportunities for high safety requirements of potential HRSV vaccine candidates.

In this example, $F_{\Delta CTD}$ was constructed by deleting amino acids 554-574 from the amino acid sequence (SEQ ID NO: 3) of F protein of HRSV A2 strain. F/vG-CTD was constructed by replacing amino acids 553-574 of SEQ ID NO:3 with amino acids 491-511 of SEQ ID NO:4 (VSV G protein (Indiana serotype)). F/vG-TM+CTD was constructed by replacing amino acids 537-551 of SEQ ID NO:3 with amino acids 476-511 of SEQ ID NO:4 (VSV G (Indiana serotype)). F504/vG447-511 was prepared by replacing amino acids 505-574 of SEQ ID NO:3 with amino acids 447-511 of SEQ ID NO:4. F504/vG447-491 was made by replacing amino acids 505-551 of SEQ ID NO:3 with amino acids 447-491 of SEQ ID NO:4.

Segments in the cytoplasmic tail or transmembrane domain of F fusion protein can also be replaced with sequences derived from other viral transmembrane proteins. These viral transmembrane proteins include, but are not limited to, envelope proteins selected from Influenza viruses (e.g., hemagglutinin), Parainfluenza viruses, HIVs, or Ebola viruses.

The invention also features incorporation of a modified RSV F fusion protein into a non-RSV envelope virus. This can be achieved by using a complementation packaging system, or by modifying the genome of the non-RSV envelope virus. In one example, the non-RSV envelope virus lacks its homologous membrane fusion protein(s). By introducing a modified F protein of the invention, transmissability of the non-RSV virus can be modulates For instance, the HRSV $F_{\Delta CTD}$ gene can be introduced into the genome of human Parainfluenza 3 virus from which homologous F protein gene is removed. The modified Parainfluenza virus has attenuated cell-to-cell transmission and therefore improved safety of use as vaccines.

The foregoing description of the invention provides illustration and description, but is not intended to be exhaustive or to limit the invention to the precise one disclosed. Modifications and variations are possible consistent with the above teachings or may be acquired from practice of the invention. Thus, it is noted that the scope of the invention is defined by the claims and their equivalents.

What is claimed is:

1. A recombinant, live, attenuated virus of the Paramyxoviridae family comprising a baculovirus GP64 envelope glycoprotein capable of mediating entry of said recombinant virus into a mammalian cell; wherein said recombinant, live, attenuated virus maintains infective stability when stored at above 0° C. for at least 3.5 days.

2. The recombinant, live, attenuated virus of claim 1, wherein the baculovirus GP64 envelope glycoprotein comprises an ectodomain and a transmembrane domain of the baculovirus GP64 glycoprotein and a C-terminal sequence of a respiratory syncytial virus fusion protein F.

3. A pharmaceutical composition comprising a therapeutically effective amount of the recombinant, live, attenuated virus of claim 1, wherein said pharmaceutical composition has been stored at above 0° C. for at least 3.5 days.

4. A pharmaceutical composition comprising the recombinant, live, attenuated virus of claim 3, wherein the composition has been stored at above 0° C. for at least 3.5 days, wherein infectivity of said recombinant, live, attenuated virus at the end of said at least 3.5 days is at least 60% of that at the beginning of said at least 3.5 days, and wherein the average infectivity of wild-type human respiratory syncytial virus A2 strain, when stored at above 0° C. for at least 3.5 days is reduced by more than 40%.

5. The recombinant, live, attenuated virus of claim 1, wherein said recombinant, live, attenuated virus further comprises or encodes an immunogenic epitope of a mammalian pathogen.

6. The recombinant, live, attenuated virus of claim 1, wherein said baculovirus GP64 envelope glycoprotein comprises a heterologous cytoplasmic tail.

7. An enveloped recombinant, live, attenuated virus of the Paramyxoviridae family comprising a heterologous envelope protein baculovirus GP64, wherein said envelope protein is capable of mediating entry of the recombinant virus into a mammalian cell, wherein the recombinant virus has been stored for at least 3.5 days, wherein infectivity of the recombinant virus at the end of said at least 3.5 days is at least 60% of that at the beginning of said at least 3.5 days, and wherein the average infectivity of a wild-type virus of the same species as the recombinant virus, when stored the same as the recombinant virus for said at least 3.5 days, is reduced by more than 40%.

8. The recombinant, live, attenuated virus of claim 7, wherein said virus has been stored at above 0° C. for said at least 3.5 days.

9. A recombinant, live, attenuated respiratory syncytial virus (RSV) comprising a baculovirus GP64 envelope glycoprotein capable of mediating entry of said recombinant RSV into a mammalian cell; wherein said envelope protein comprises an ectodomain of a baculovirus envelope GP64 protein; wherein said recombinant RSV lacks endogenous RSV small hydrophobic protein; and wherein said recombinant RSV maintains infectivity after storage at temperature or temperatures at above 0° C. cumulatively for at least 3.5 days.

* * * * *

SEQUENCE LISTING

<160> NUMBER OF SEQ ID NOS: 4

<210> SEQ ID NO 1
<211> LENGTH: 7
<212> TYPE: PRT
<213> ORGANISM: Autographa californica nucleopolyhedrovirus

<400> SEQUENCE: 1

```
Arg Asn Arg Asn Arg Gln Tyr
1               5
```

<210> SEQ ID NO 2
<211> LENGTH: 15
<212> TYPE: PRT
<213> ORGANISM: Human respiratory syncytial virus

<400> SEQUENCE: 2

```
Ser Arg Arg Gln Leu Ser Gly Ile Asn Asn Ile Ala Phe Ser Asn
1               5                   10                  15
```

<210> SEQ ID NO 3
<211> LENGTH: 574
<212> TYPE: PRT
<213> ORGANISM: Human respiratory syncytial virus

<400> SEQUENCE: 3

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Pro Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240
```

```
Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
                340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Ile Asn Leu Cys Asn Val
        370                 375                 380

Asp Ile Phe Asn Pro Lys Tyr Asp Cys Lys Ile Met Thr Ser Lys Thr
385                 390                 395                 400

Asp Val Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Met Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 4
<211> LENGTH: 511
<212> TYPE: PRT
<213> ORGANISM: Vesicular stomatitis virus

<400> SEQUENCE: 4

Met Lys Cys Leu Leu Tyr Leu Ala Phe Leu Phe Ile Gly Val Asn Cys
1               5                   10                  15

Lys Phe Thr Ile Val Phe Pro His Asn Gln Lys Gly Asn Trp Lys Asn
            20                  25                  30

Val Pro Ser Asn Tyr His Tyr Cys Pro Ser Ser Ser Asp Leu Asn Trp
        35                  40                  45
```

-continued

```
His Asn Asp Leu Ile Gly Thr Ala Ile Gln Val Lys Met Pro Lys Ser
     50                  55                  60
His Lys Ala Ile Gln Ala Asp Gly Trp Met Cys His Ala Ser Lys Trp
 65                  70                  75                  80
Val Thr Thr Cys Asp Phe Arg Trp Tyr Gly Pro Lys Tyr Ile Thr Gln
                 85                  90                  95
Ser Ile Arg Ser Phe Thr Pro Ser Val Glu Gln Cys Lys Glu Ser Ile
            100                 105                 110
Glu Gln Thr Lys Gln Gly Thr Trp Leu Asn Pro Gly Phe Pro Pro Gln
            115                 120                 125
Ser Cys Gly Tyr Ala Thr Val Thr Asp Ala Glu Ala Val Ile Val Gln
        130                 135                 140
Val Thr Pro His His Val Leu Val Asp Glu Tyr Thr Gly Glu Trp Val
145                 150                 155                 160
Asp Ser Gln Phe Ile Asn Gly Lys Cys Ser Asn Tyr Ile Cys Pro Thr
                165                 170                 175
Val His Asn Ser Thr Thr Trp His Ser Asp Tyr Lys Val Lys Gly Leu
            180                 185                 190
Cys Asp Ser Asn Leu Ile Ser Met Asp Ile Thr Phe Phe Ser Glu Asp
        195                 200                 205
Gly Glu Leu Ser Ser Leu Gly Lys Glu Gly Thr Gly Phe Arg Ser Asn
210                 215                 220
Tyr Phe Ala Tyr Glu Thr Gly Gly Lys Ala Cys Lys Met Gln Tyr Cys
225                 230                 235                 240
Lys His Trp Gly Val Arg Leu Pro Ser Gly Val Trp Phe Glu Met Ala
                245                 250                 255
Asp Lys Asp Leu Phe Ala Ala Ala Arg Phe Pro Glu Cys Pro Glu Gly
            260                 265                 270
Ser Ser Ile Ser Ala Pro Ser Gln Thr Ser Val Asp Val Ser Leu Ile
        275                 280                 285
Gln Asp Val Glu Arg Ile Leu Asp Tyr Ser Leu Cys Gln Glu Thr Trp
290                 295                 300
Ser Lys Ile Arg Ala Gly Leu Pro Ile Ser Pro Val Asp Leu Ser Tyr
305                 310                 315                 320
Leu Ala Pro Lys Asn Pro Gly Thr Gly Pro Ala Phe Thr Ile Ile Asn
                325                 330                 335
Gly Thr Leu Lys Tyr Phe Glu Thr Arg Tyr Ile Arg Val Asp Ile Ala
            340                 345                 350
Ala Pro Ile Leu Ser Arg Met Val Gly Met Ile Ser Gly Thr Thr Thr
        355                 360                 365
Glu Arg Glu Leu Trp Asp Asp Trp Ala Pro Tyr Glu Asp Val Glu Ile
370                 375                 380
Gly Pro Asn Gly Val Leu Arg Thr Ser Ser Gly Tyr Lys Phe Pro Leu
385                 390                 395                 400
Tyr Met Ile Gly His Gly Met Leu Asp Ser Asp Leu His Leu Ser Ser
                405                 410                 415
Lys Ala Gln Val Phe Glu His Pro His Ile Gln Asp Ala Ala Ser Gln
            420                 425                 430
Leu Pro Asp Asp Glu Ser Leu Phe Phe Gly Asp Thr Gly Leu Ser Lys
        435                 440                 445
Asn Pro Ile Glu Leu Val Glu Gly Trp Phe Ser Ser Trp Lys Ser Ser
450                 455                 460
```

-continued

```
Ile Ala Ser Phe Phe Phe Ile Ile Gly Leu Ile Ile Gly Leu Phe Leu
465                 470                 475                 480

Val Leu Arg Val Gly Ile His Leu Cys Ile Lys Leu Lys His Thr Lys
                485                 490                 495

Lys Arg Gln Ile Tyr Thr Asp Ile Glu Met Asn Arg Leu Gly Lys
            500                 505                 510
```